US008664365B2

(12) United States Patent
Luehrsen et al.

(10) Patent No.: US 8,664,365 B2
(45) Date of Patent: Mar. 4, 2014

(54) ANTIBODIES TO EPHA3

(75) Inventors: Kenneth Luehrsen, Half Moon Bay, CA (US); David Martinez, Sunnyvale, CA (US); Christina Yi, San Francisco, CA (US); Christopher R. Bebbington, San Mateo, CA (US); Geoffrey T. Yarranton, Burlingame, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 395 days.

(21) Appl. No.: 12/904,953

(22) Filed: Oct. 14, 2010

(65) Prior Publication Data

US 2011/0123549 A1 May 26, 2011

Related U.S. Application Data

(60) Provisional application No. 61/251,668, filed on Oct. 14, 2009.

(51) Int. Cl.
*C12P 21/08* (2006.01)

(52) U.S. Cl.
USPC ........................................ 530/387.3

(58) Field of Classification Search
None
See application file for complete search history.

(56) References Cited

U.S. PATENT DOCUMENTS

2005/0255552 A1 11/2005 Flynn et al.
2006/0134098 A1 6/2006 Bebbington et al.

FOREIGN PATENT DOCUMENTS

WO WO 2008/112192 9/2008
WO WO 2010/102244 9/2010

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
International Search Report and Written Opinion dated Feb. 15, 2011, issued in related International Patent Application No. PCT/US2010/052725, filed Oct. 14, 2010.
Arruga et al., "EphA3 is abnormally expressed in Chronic myeloprolipherative disorders and could represents a new molecular target," Proceedings of the Annual Meeting of the American Association for Cancer Research, 2009, vol. 50, No. 1, pp. 692.
Cilloni et al., "EphA3 Kinase is Constitutively Activated in Chronic Myeloid Leukemia during Progression to Accelerated and Blast Crisis and It Could Represented a New Molecular Target," 2008, Blood, vol. 112, No. 11, pp. 399.
List et al., "Development Therapeutics for MDS," 2009, Leukemia Research, vol. 33, No. Suppl. 1, pp. S27-S28.
Vearing et al., "Concurrent binding and anti-EphA3 antibody and ephrin-A5 amplifies EphA3 signaling and downstream responses: Potential as EphA3-specific tumor-targeting reagents," 2005, Cancer Research, vol. 65, No. 15, 6745-6754.
Yamane-Ohnuki et al., "Establishment of FUT8 knockout Chinese hamster ovary cells: an ideal host cell line for producing completely defucosylated antibodies with enhanced antibody-dependent cellular cytotoxicity," 2004, Biotechnol Bioeng., vol. 87, No. 5, 614-622.
"Study of KB004 in Subjects with Hematologic Malignancies," ClinicalTrials.gov, Sep. 21, 2010, retrieved from the Internet: URL: http://clinicaltrials.gov/ct2/show/NCT01211691.

* cited by examiner

*Primary Examiner* — Brad Duffy
(74) *Attorney, Agent, or Firm* — Kilpatrick Townsend & Stockton LLP

(57) ABSTRACT

The current invention relates to high-affinity antibodies to EphA3 that have reduced immunogenicity when administered to a human to treat diseases and method of using such antibodies.

29 Claims, 7 Drawing Sheets

Figure 1

Heavy chain V-regions

| SEQ ID: | |
|---|---|
| 1 | QVQLVQSGAEVKKPGTSVKVSCKASGYTFTGYWMNWVRQASGQGLEWMGDIYPGSGNTNYDEKFQGRVTMTRDTSISTAYMELSRLRSDDTAVYYCARSGVYEDFDSWGQGTTVTVSS |
| 2 | QVQLVQSGAEVKKPGASVKVSCKASGYTFTGYWMNWVRQAPGQGLEWMGDIYPGSGNTNYDEKFQGRVTMTRDTSISTAYMELSRLRSDDTAVYYCARSGYYEEFDSWGQGTTVTVSS |
| 3 | QVQLVQSGAEVKKPGTSVKVSCKASGYTFTGYWMNWVRQASGQGLEWMGDIYPGSGNTNYDEKFQGRVTMTRDTSISTAYMELSRLRSDDTAVYYCARSGYYEEFDSWGQGTTVTVSS |
| 4 | QVQLVQSGAELKKPGASVKVSCKTSGYTFTGYWMNWVRQAPGQGLEWMGDIYPGSGNTNYDEKFQGRVTMTRDTSISTAYMELSRLRSDDTAVYYCARSGYYEEFDSWGQGTTVTVSS |
| 5 | QVQLVQSGAEVKKPGASVKVSCKASGYTFTGYWMNWVRQAPGQGLEWMGDIYPGSGNTNYDEKFQGRVTMTRDTSISTAYMELSRLRSDDTAVYYCARGGYYEDFDSWGQGTTVTVSS |
| 6 | EVQLVQSGAEVKKPGESLRISCKGSGYTFTTYWISWVRQMPGQGLEWMGDIYPGSGNTNYAQKFQGRVTITADKSTSTAYMGLSSLRSEDTAVYYCARSGYYEDFDSWGQGTTVTVSS |
| 7 | EVQLVQSGAEVKKPGESLRISCKGSGYTFTTYWISWVRQMPGQGLEWMGDIYPGSGNTNYAQEFRGRVTITADESTSTAYVELSSLRSEDTAVYYCARSGYYEDFDSWGQGTTVTVSS |
| 8 | EVQLVQSGAEVKKPGESLRISCKGSGYTFTTYWISWVRQMPGQGLEWMGDIYPGSGNTNYAQKFLGRVTITADESTSTAYMELSSLRYDDTAVYYCARSGYYEDFDSWGQGTTVTVSS |
| 9 | EVKLEESGAELVKPGSSVKLSCKASGYNFTSYWINWVRLRPGQGLEWIGDIYPGSGNTNYDEKFKRKATLTVDTSSSTAYMQLSSLASEDTAVYYCARSGYYEDFDVWGQGTTVTVSS |
| 10 | EVKLEESGAELVKPGSSVKLSCKASGYNFTSYWINWVRLRPGQGLEWIGDIYPGSGNTNYDEKFKRKATLTVDTSSSTAYMQLSSLASEDTAVYYCARSGYYEDFDIWGQGTMVTVSS |

Figure 1-con't

Light chain V-regions

| SEQ ID | |
|---|---|
| 11 | DIQMTQSPSFLSASVGDRVTITCRASQGIISYLAWYQQKPEKAPKRLIYAASSLQSGVPSRFSGSGSGTEFTLTISSLQPEDFATYYCVQYANYPYTFGQGTKLEIK |
| 12 | DIQMTQSPSFLSASVGDRVTITCRASQGIISYLAWYQQKPEKAPKRLIYAASSLQSGVPSRFSGSGSGTEFTLTISSLQPEDFATYYCVQYSNYPYTFGQGTKLEIK |
| 13 | DIQMTQSPSFLSASVGDRVTITCRASQGIISYLAWYQQKPEKAPKRLIYAASSLQSGVPSRFSGSGSGTEFTLTISSLQPEDFATYYCGQYANYPYTFGQGTKLEIK |
| 14 | DIQMTQSPSFLSASVGDRVTITCRASQGIISYLAWYQQKPEKAPKRLIYAASSLQSGVPSRFSGSGSGTEFTLTISSLQPEDFATYYCVQYANYPYTFGQGTKLEIK |
| 15 | DIQLTQSPSFLSASVGDRVTITCRASQGIISYLAWYQQKPEKAPKRLIYGASSLQSGVPSRFSGSGSGTEFTLTISSLQPEDFATYYCVQYANYPYTFGQGTKLEIK |
| 16 | DIQMTQSPSSLSASLGDRVTITCQASQDISTYLNWIQQKPGKAPKRLIYAASSLQSGVPSRFSGSGSGTEFTLTISSLQPEDFATYYCVQYANYPYTFGQGTKLEIK |
| 17 | DIQMTQSPSSLSASLGDRVTITCQASQDISTYLNWIQQKPGKAPKRLIYAASSLQRGVPSRFSGSGSGTEFTLTISSLQPEDFATYYCVQYANYPYTFGQGTKLEIK |
| 18 | DIQMTQSPSSLSASVGDRVTITCRASQSISSYLAWYQQKPGKAPKRLIYAASSLQRGVPSRFSGSGSGTEFTLTISSLQPEDFATYYCVQYANYPYTFGQGTKLEIK |
| 19 | DIQMTQSPSFLSASVGDRVTITCRASQGIISYLAWYQQKPEKAPKRLIYAASSLQSGVPSRFSGSGSGTEFTLTISSLQPEDFATYYCAQYANYPYTFGQGTKLEIK |
| 20 | DIQMTQSPSFLSASVGDRVTITCRASQGIISYLAWYQQKPEKAPKRLIYAASSLQSGVPSRFSGSGSGTEFTLTISSLQPEDFATYYCVQYAKYPYTFGQGTKLEIK |
| 21 | DIQMTQSPSFLSASVGDRVTITCRASQGIISYLAWYQQKPEKAPKRLIYAASSLQSGVPSRFSGSGSGTEFTLTISSLQPEDFATYYCVGYANYPYTFGQGTKLEIK |
| 22 | DIQMTQSPSFLSASVGDRVTITCRASQGIISYLAWYQQKPEKAPKRLIYAASSLQSGVPSRFSGSGSGTEFTLTISSLQPEDFATYYCVRYANYPYTFGQGTKLEIK |
| 23 | DIQMTQSPSFLSASVGDRVTITCRASQGIISYLAWYQQKPEKAPKRLIYAASSLQSGVPSRFSGSGSGTEFTLTISSLQPEDFATYYCVQYLNYPYTFGQGTKLEIK |

ANTIBODIES TO EPHA3

CROSS-REFERENCE TO RELATED APPLICATIONS

This application claims benefit of U.S. provisional application No. 61/251,668, filed Oct. 14, 2009, which application is herein incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -36-1.TXT, created on Aug. 13, 2013, 77,824 bytes, machine format IBM-PC, MS-Windows operating system, is hereby incorporated by reference in its entirety for all purposes.

BACKGROUND OF THE INVENTION

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov, A., et al., *Dev Cell* 7:465-80 (2004)). In contrast to other receptor tyrosine kinases, Eph receptor activation does not only require ligand binding and dimerization but also involves preformed ligand oligomers. Thus, tyrosine phosphorylation of Eph receptors requires presentation of ephrin ligands in their clustered or membrane-attached forms (Davis et al., *Science* 266:816-819 (1994)). Functional and biochemical Eph responses occur at higher ligand oligomerization states (Stein et al., *Genes Dev* 12:667-678 (1998)).

Among other patterning functions, various Ephs and ephrins have been shown to play a role in vascular development. The de-regulated re-emergence of some ephrins and their receptors in adults also has been observed to contribute to tumor invasion, metastasis and neo-angiogenesis. For example, dominant-negative, soluble EphA2 or A3 proteins exhibit effects on ephrin-induced endothelial cell function in vitro, and tumor angiogenesis and progression in vivo (Nakamoto, et al., *Microsc Res Tech* 59:58-67 (2002); Brantley-Sieders, et al., *Curr Pharm Des* 10:3431-42 (2004); Brantley, et al. *Oncogene* 21:7011-26 (2002); Cheng, et al. *Neoplasia* 5:445-56 (2003). Dobrzanski, et al. *Cancer Res* 64:910-9 (2004)). Furthermore, Eph family members have been found to be over-expressed on tumor cells from a wide variety of human solid tumors (Brantley-Sieders, et al., *Curr Pharm Des* 10:3431-42 (2004); Marme, D. Ann *Hematol* 81 Suppl 2:S66 (2002); Booth, C. et al., *Nat Med* 8:1360-1 (2002)).

Epha3 has also been reported to be activated and overexpressed on $CD34^+$ cells in chronic myeloid leukemia (CML) patients in the accelerated phase and blast crisis stage (Cilloni et al., American Society of Hematology, Abstract 1092, 2008 (available on line Nov. 14, 2008)). Cilloni et al. reported that when primary CML cells or EphA3-transfected normal cells were incubated with a specific monoclonal antibody, the antibody induced a significant reduction of proliferation in primary cells and transfected cells, reduced colony growth and induced changes to the adhesion properties. The antibody did not induce any significant changes in normal control cells or cells from CML patient in the chronic stage.

This invention is based, in part, on the discovery of new anti-EphA3 antibodies.

BRIEF SUMMARY OF THE INVENTION

The invention is directed to potent anti-EphA3 antibodies and methods of using such antibodies, e.g., for the treatment of a disease involving EphA3. An antibody of the invention has the characteristics as described herein. Thus, in one aspect, an antibody of the invention comprises a $V_H$ region that comprises a CDR3 comprising the amino acid sequence $X_1GX_2YEX_3FDX_4$ (SEQ ID NO:38), wherein $X_1$ is S or G, $X_2$ is Y or V, $X_3$ is E or D, and $X_4$ is S, V, or I, with the proviso that when the amino acid sequence is SGYYEDFDS (SEQ ID NO:39) the CDR1 is not SYWIN (SEQ ID NO:40) and when the amino acid sequence is SGYYEEFDS (SEQ ID NO:41) the CDR1 is not TYWIS (SEQ ID NO:42). In some embodiments, the antibody has a CDR3 that comprises the amino acid sequence GGYYEDFDS (SEQ ID NO:43), SGYYEEFDS (SEQ ID NO:41), SGVYEDFDS (SEQ ID NO:44), SGYYEDFDV (SEQ ID NO:45), or SGYYEDFDI (SEQ ID NO:46). In some embodiments, the antibody has a J segment that comprises at least 80% identity, typically at 85%, or at least 90% identity, to a human germline J segment amino acid sequence; or that differs from a human germline J segment at no more than two positions; and a V-segment that comprises at least 80% identity, typically at least 85% identity, and preferably 90% identity, or greater, to a human germ line V-segment amino acid sequence. In some embodiment, the J segment comprises at least 90% identity to human JH6 amino acid sequence, and the V-segment comprises at least 90% identity to a human VH1 1-02 amino acid sequence. In some embodiments, the antibody has an FR4 that comprises WGQGTTVTVSS (SEQ ID NO:47), or an FR4 that differs no more than one amino acid from WGQGTTVTVSS (SEQ ID NO:47). In some embodiments, the antibody comprises a $V_H$ CDR1, or a $V_H$ CDR2, or both a $V_H$ CDR1 and a $V_H$ CDR2, as shown in a $V_H$ region set forth in FIG. 1. For example, an antibody of the invention can have a $V_H$ CDR1 that has the amino acid sequence GYWMN (SEQ ID NO:48), TYWIS (SEQ ID NO:42), or SYWIN (SEQ ID NO:40) and/or a CDR2 that has the amino acid sequence DIYPGSGNTNYDEKFQG (SEQ ID NO:49), DIYPGSGNTNYAQKFQG (SEQ ID NO:50), DIYPGSGNTNYAQEFRG (SEQ ID NO:51), DIYPGSGNTNYAQKFLG (SEQ ID NO:52), DIYPGSGNTNYDEKFEG (SEQ ID NO:53), or DIYPGSGNTNYDEKFKR (SEQ ID NO:54). In some embodiments, the antibody has a $V_H$ CDR1 GYWMN (SEQ ID NO:48) and a CDR2 DIYPGSGNTNYDEKFQG (SEQ ID NO:49). In some embodiments, the antibody has a $V_H$ CDR1 TYWIS (SEQ ID NO:42) and a $V_H$ CDR2 DIYPGSGNTNYAQ(K/E)F(Q/R/L)G (SEQ ID NO:55). In some embodiments, an antibody of the invention has the $V_H$ CDR1, CDR2, and CDR3 from one of the V regions as shown in FIG. 1. In some embodiments, the antibody has a $V_H$ V-segment amino acid sequence of a V-segment sequence shown in FIG. 1. In some embodiments, the $V_H$ has the sequence of a $V_H$ region set forth in FIG. 1.

The invention also provides an antibody that has a $V_L$ region that comprises a CDR3 binding specificity determinant having the sequence $X_1X_2YX_3X_4YPYT$ (SEQ ID NO:56), wherein $X_1$ is G, V, or A; $X_2$ is Q, R, or G; $X_3$ is A, S, or L; and $X_4$ is N or K. In some embodiments, the CDR3 comprises GQYANYPYT (SEQ ID NO:57), VQYAKYPYT (SEQ ID NO:58), AQYANYPYT (SEQ ID NO:59), VQYSNYPYT (SEQ ID NO:60), VQYANYPYT (SEQ ID NO:61), VGYANYPYT (SEQ ID NO:62), VRYANYPYT (SEQ ID NO:63), or VQYLNYPYT (SEQ ID NO:64). In some embodiments, when the CDR3 is VQYANYPYT (SEQ ID NO:61), the CDR1 is not RASQEISGYLG (SEQ ID NO:65), or RASQGIISYLA (SEQ ID NO:66) and/or the CDR2 is not AASTLDS (SEQ ID NO:67) or AASSLQS (SEQ ID NO:68). In some embodiments, the $V_L$ region comprises a J segment that comprises at least 80% identity, typically at least 85% or 90% identity, to a human germline J segment amino acid sequence, or that differs no more than two amino acids from a human germline segment; and a V-segment that comprises at least 80% identity, typically at least 90% identity, or greater, to a human germ line V-segment amino acid sequence. In some embodiments, the J segment has no more than two amino acid changes, often no more than one amino acid change, relative to the sequence FGQGTKLEIK (SEQ ID NO:69) from the human germ-line Jκ2 amino acid sequence and the V-segment comprises at least 90% identity to human germline JκI L15 amino acid sequence. In some embodiments, the FR4 of the antibody has the amino acid sequence FGQGTKLEIK (SEQ ID NO:69), or has no more than one amino acid residue changed relative to the sequence FGQGTKLEIK (SEQ ID NO:69). In some embodiments, the $V_L$ region comprises a CDR1, or a CDR2, or both a CDR1 and CDR2 of a sequence VL region shown in FIG. 1. For example, a CDR1 can have the sequence RASQGIISYLA (SEQ ID NO:66), QASQDISTYLN (SEQ ID NO:70), RASQEISGYLG (SEQ ID NO:65), or RASQSISSYLA (SEQ ID NO:71); and/or a CDR2 can have the sequence AASSLQS (SEQ ID NO:68), GASSLQS (SEQ ID NO:72), AASSLQR (SEQ ID NO:73), or AASTLDS (SEQ ID NO:67). In some embodiments, the CDR1 has the sequence RASQGIISYLA (SEQ ID NO:66) and the CDR2 has the sequence GASSLQS (SEQ ID NO:72). In some embodiments, the CDR1 has the sequence QASQDISTYLN (SEQ ID NO:70) and the CDR2 has the sequence AASSLQR (SEQ ID NO:73) or AASSLQS (SEQ ID NO:68). In some embodiments, the CDR1 has the sequence RASQSISSYLA (SEQ ID NO:71) and the CDR2 has the sequence AASSLQR (SEQ ID NO:73). In some embodiments, the $V_L$ region comprises the CDR1, CDR2, and CDR3 of one of the $V_L$ regions set forth in FIG. 1. In some embodiments, the $V_L$ region comprises a V-segment that has a V-segment sequence as shown in FIG. 1. In some embodiments, the $V_L$ region has the sequence of a $V_L$ region set forth in FIG. 1. In typical embodiments, the $V_H$ region of the antibody comprises any of the $V_H$ regions described in the preceding paragraph.

In some embodiments, the invention provide an antibody that comprises a $V_L$ region that has a CDR3 comprising GQYANYPYT (SEQ ID NO:57), VQYAKYPYT (SEQ ID NO:58), AQYANYPYT (SEQ ID NO:59), VQYSNYPYT (SEQ ID NO:60), VGYANYPYT (SEQ ID NO:61), VRYANYPYT (SEQ ID NO:63), or VQYLNYPYT (SEQ ID NO:64). In some embodiments, the antibody comprises a heavy chain CDR3 comprising the amino acid sequence $X_1GX_2YEX_3FDX_4$ (SEQ ID NO:38), wherein $X_1$ is S or G, $X_2$ is Y or V, $X_3$ is E or D, and $X_4$ is 5, V, or I. In some embodiments. In some embodiments, the heavy chain CDR3 comprises the amino acid sequence GGYYEDFDS (SEQ ID NO:43), SGYYEEFDS (SEQ ID NO:41), SGVYEDFDS (SEQ ID NO:44), SGYYEDFDV (SEQ ID NO:45), or SGYYEDFDI (SEQ ID NO:46). In some embodiments, the antibody comprises a light chain CDR1 or CDR2 set forth in FIG. 1, or a heavy chain CDR1 or CDR2 set forth in FIG. 1. In some embodiments, the antibody comprises a light chain CDR1 and CDR2 as set forth in FIG. 1 and/or a heavy chain CDR1 and CDR2 set forth in FIG. 1. In some embodiments, the antibody comprises a $V_L$ V-segment set forth in FIG. 1.

The invention additionally provides an antibody that comprises a $V_H$ region comprising a CDR3 having the sequence SGYYE(E/D)FDS (SEQ ID NO:74) and a $V_L$ region CDR3 sequence set forth in the preceding paragraph, with the proviso that the $V_L$ region CDR3 sequence is not VQYANYPYT (SEQ ID NO:61) or VQYMNYPYT (SEQ ID NO:75). In some embodiments, the antibody comprises a heavy chain CDR1 or CDR2 set forth in FIG. 1, or a light chain CDR1 or CDR2 set forth in FIG. 1. In some embodiments, the antibody comprises a heavy chain CDR1 and CDR2 as set forth in FIG. 1 and/or a light chain CDR1 and CDR2 set forth in FIG. 1.

In some embodiments, an anti-EphA3 antibody of the invention comprises the $V_H$ CDR1, CDR2, and CDR3 from one of the $V_H$ regions set forth in FIG. 1 and the $V_L$ CDR1, CDR2, and CDR3 from one of the $V_L$ regions set forth in FIG. 1.

An antibody of the invention can comprise a $V_H$ region as set forth in FIG. 1 or a $V_L$ region as set forth in FIG. 1. Often, the antibody comprises a $V_H$ region as set forth in FIG. 1 and a $V_L$ region as set forth in FIG. 1. In some embodiments, the antibody comprises a combinations of $V_H$ and $V_L$ regions that comprise: a) SEQ ID NO:1 and SEQ ID NO:20, b) SEQ ID NO:2 and SEQ ID NO:11, c) SEQ ID NO: 2 and SEQ ID NO:12, d) SEQ ID NO:2 and SEQ ID NO:19, e) SEQ ID NO:2 and SEQ ID NO:21, f) SEQ ID NO:2 and SEQ ID NO:22, g) SEQ ID NO:2 and SEQ ID NO:23, h) SEQ ID NO:3 and SEQ ID NO:11, i) SEQ ID NO:3 and SEQ ID NO:12, j) SEQ ID NO:3 and SEQ ID NO:21, k) SEQ ID NO:3 and SEQ ID NO:22, l) SEQ ID NO:4 and SEQ ID NO:11, m) SEQ ID NO:4 and SEQ ID NO:13, n) SEQ ID NO:5 and SEQ ID NO:11, o) SEQ ID NO:5 and SEQ ID NO:13, p) SEQ ID NO:5 and SEQ ID NO:21, q) SEQ ID NO:6 and SEQ ID NO:14, r) SEQ ID NO:6 and SEQ ID NO:15, s) SEQ ID NO:7 and SEQ ID NO:14, t) SEQ ID NO:7 and SEQ ID NO:15, u) SEQ ID NO:8 and SEQ ID NO:14, v) SEQ ID NO:8 and SEQ ID NO:15, w) SEQ ID NO:9 and SEQ ID NO:16, x) SEQ ID NO:9 and SEQ ID NO:17, y) SEQ ID NO:9 and SEQ ID NO:19, z) SEQ ID NO:10 and SEQ ID NO:17, aa) SEQ ID NO:10 and SEQ ID NO:18, or bb) SEQ ID NO:10 and SEQ ID NO:20.

In some embodiments, an antibody of the invention, e.g., that has a $V_H$ region sequence selected from the $V_H$ region sequences in FIG. 1 and a $V_L$ region selected from the $V_L$ region sequences in FIG. 1, has a monovalent affinity better than about 10 nM, and often better than about 5 nM or 1 nM as determined by surface plasmon resonance analysis performed at 37° C. Thus, in some embodiments, the antibodies of the invention have an affinity (as measured using surface plasmon resonance) of about 10 nM, about 5 nM, about 2.5 nM, about 1 nM, about 0.5 nM, about 0.25 nM, or about 0.1 nM, or better.

An antibody of the invention as described herein may have a $V_H$ region and/or a $V_L$ region that comprises a methionine at the N-terminus.

In some embodiments, the antibody is an IgG. In some embodiments, the antibody is an IgG1 or an IgG3. In some embodiments, the antibody is an IgG2 or an IgG4.

In some embodiments, the antibody comprises a heavy chain constant regions having the amino acid sequence set forth in SEQ ID NO:24 and/or a kappa light chain constant region having the amino acid sequence set forth in SEQ ID NO:25.

In some embodiments, the heavy chain constant region of an antibody is afucosylated. In some embodiments, an antibody preparation comprising an antibody of the invention is hypofucosylated or afucosylated.

In some embodiments, an anti-EphA3 antibody of the invention has a heavy chain amino acid sequence and a light chain amino acid sequence that comprises SEQ ID NO:26 and SEQ ID NO:27, SEQ ID NO:28 and SEQ ID NO:29, SEQ ID NO:30 and SEQ ID NO:31, SEQ ID NO:32 and SEQ ID NO:33, SEQ ID NO:34 and SEQ ID NO:35, or SEQ ID NO:36 and SEQ ID NO:27, respectively; and the antibody is afucosylated.

In some embodiments, the antibody is a $(Fab')_2$.

In some embodiments the antibody is PEGylated.

In some embodiments, the antibody activates EphA3.

In some embodiments, the antibody does not compete with a natural ligand, e.g., ephrin A5, for binding to EphA3.

In another aspect, the invention provides a method of treating a patient that has an EphA3-dependent disease, the method comprising administering an antibody of the invention as described herein to the patient in a therapeutically effective amount. The patient may, e.g., have a cancer. In some embodiments, the antibody is administered to a patient that has a solid tumor that comprises tumor cells that express EphA3. In other embodiments, the antibody is administered to a patient that as a tumor that does not have tumor cells that express EphA3.

In some embodiments, the antibody is administered to a patient that has a myeloproflierative disorder. In some embodiments, the antibody is administered to a patient that has acute myeloid leukemia or chronic myeloid leukemia. In some some embodiments, the antibody is administered to a patient that has a lymphoma. In some embodiments, the antibody is administered to a patient that has myelodysplastic syndrome, polycythemia vera, essential thrombocythemia, or idiopathic myelofibrosis.

BRIEF DESCRIPTION OF THE DRAWINGS

FIG. 1 provides exemplary $V_H$ (SEQ ID NOS:1-10) and $V_L$ (SEQ ID NOS:11-23) sequences of anti-EphA3 antibodies of the invention.

DETAILED DESCRIPTION OF THE INVENTION

Figure 2:
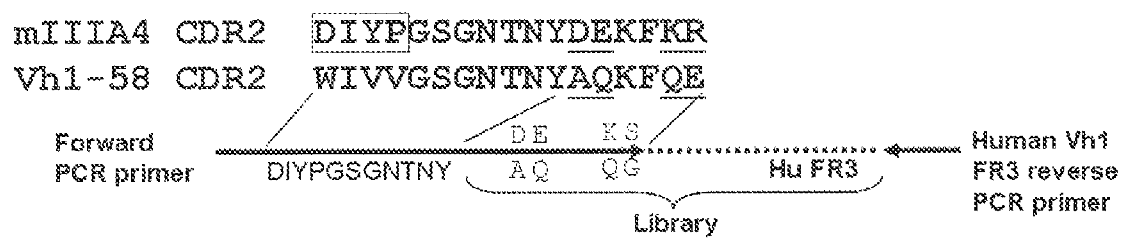
FIG. 2 provides a schematic of a heavy chain CDR2/FR3 cassette construction (SEQ ID NOS:54, 76 and 77).

As used herein "EphA3" refers to the Eph receptor A3. This receptor has also been referred to as "Human embryo kinase", "hek", "eph-like tyrosine kinase 1", "etkl" or "tyro4". EphA3 belongs to the ephrin receptor subfamily of the protein-tyrosine kinase family. EPH and EPH-related receptors have been implicated in mediating developmental events. Receptors in the EPH subfamily typically have a single kinase domain and an extracellular region containing a Cys-rich domain and 2 fibronectin type III repeats. The ephrin receptors are divided into 2 groups based on the similarity of their extracellular domain sequences and their affinities for binding ephrin-A and ephrin-B ligands. EphA3 binds ephrin-A ligands. EphA3 nucleic acid and protein sequences are known. An exemplary human EphA3 amino acid sequence is available under accession number (EAW68857).

In the present invention, "activation" of EphA3 causes phosphorylation of EphA3. An antibody that activates EphA3, i.e., causes phosphorylation of EphA3, is therefore considered to be an agonist in the context of this invention. EphA3 can be activated by dimerization. Such activation can lead to phosphorylation and apoptosis, although not necessarily to cell rounding. Activation, e.g., when clustering of EphA3 occurs, can additionally lead to morphological changes, typically rounding of the cell.

In the present invention, "EphA3 antibody" or "anti-EphA3 antibody" are used interchangeably to refer to an antibody that specifically binds to EphA3. In some embodiments, the antibody can dimerize EphA3. The term encompasses antibodies that bind to EphA3 in the presence of ephrin ligand (e.g., ephrin A5) binding, as well as antibodies that bind to the ligand binding site and compete with ligand binding to EphA3.

An "EphA3 antibody that binds to EphA3 in the presence of binding of an ephrin ligand" refers to an antibody that does not significantly prevent binding of an ephrin ligand, such as ephrin A5, to EphA3. The presence of such an antibody in a binding reaction comprising EphA3 and an ephrin ligand, e.g., ephrin A5, reduces ephrin ligand binding to EphA3 by less than about 30%, typically less than 20% or 10%.

The term "mAb IIIA4" refers to monoclonal antibody IIIA4 that was originally raised against LK63 human acute pre-B leukemia cells to affinity isolate EphA3 (Boyd, et al. *J Biol Chem* 267:3262-3267, 1992). mAb IIIA4 binds to the native EphA3 globular ephrin-binding domain (e.g., Smith, et al., *J. Biol. Chem* 279:9522-9531, 2004). It is deposited in the European Collection of Animal Cell Cultures under accession no. 91061920 (see, e.g., EP patent no. EP0590030).

An "antibody having an active isotype" as used herein refers to an antibody that has a human Fc region that binds to an Fc receptor present on immune effector cells. "Active isotypes" include IgG1, IgG3, IgM, IgA, and IgE. The term encompasses antibodies that have a human Fc region that comprises modifications, such as mutations or changes to the sugar composition and/or level of glycosylation, that modulate Fc effector function.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises munoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990).

The term "equilibrium dissociation constant" or "affinity" abbreviated ($K_D$), refers to the dissociation rate constant ($k_d$, time divided by the association rate constant ($k_a$, time$^{-1}$ M$^{-1}$). Equilibrium dissociation constants can be measured using any known method in the art. The antibodies of the present invention are high affinity antibodies. Such antibodies have a monovalent affinity better (less) than about 50 nM and often less than about 10 nM as determined by surface plasmon resonance analysis performed at 37° C. Thus, in some embodiments, the antibodies of the invention have an affinity (as measured using surface plasmon resonance) of less than about 50 nM, typically less than about 25 nM, or even less than 10 nM, e.g., about 5 nM or about 1 nM. In the context of the invention, an affinity is "better" if it has a higher affinity, e.g., as evidenced by a lower numerical $K_D$.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody typically binds to EphA3 with an affinity that is at least 100-fold greater than its affinity for other antigens.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. *Proc. Nat. Acad. Sci. USA,* 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. A germline J-segment is encoded by an immunoglobulin J-gene segment.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.,* 262 (5), 732-745 (1996); and Martin et al, *Proc. Natl Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci USA* 91: 969, 1994).

A "Humaneered™" antibody in the context of this invention refers to an engineered human antibody having a binding specificity of a reference antibody. A "Humaneered™" antibody for use in this invention has an immunoglobulin molecule that contains minimal sequence derived from a donor immunoglobulin. Typically, an antibody is "Humaneered™" by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. Methods for humaneering are provided in US patent application publication no. 20050255552 and US patent application publication no. 20060134098.

The term "binding specificity determinant" or "BSD" as used in the context of the current invention refers to the minimum contiguous or non-contiguous amino acid sequence within a CDR region necessary for determining the binding specificity of an antibody. In the current invention, the minimum binding specificity determinants reside within a portion or the full-length of the CDR3 sequences of the heavy and light chains of the antibody.

A "human" antibody as used herein encompasses humanized and Humaneered™ antibodies, as well as human monoclonal antibodies that are obtained using known techniques.

A "hypofucosylated" antibody preparation refers to an antibody preparation in which less than 50% of the oligosaccharide chains contain α1,6-fucose. Typically, less than about 40%, less than about 30%, less than about 20%, less than about 10%, or less than 5% or less than 1% of the oligosaccharide chains contain α1,6-fucose in a "hypofucosylated" antibody preparation.

An "afucosylated" antibody lacks α1,6-fucose in the carbohydrate attached to the CH2 domain of the IgG heavy chain.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

An EphA3-dependent disease, as used herein, refers to a disease in which a cell that expresses EphA3 is a target for therapy to treat the disease.

The term "vasculogenic bone marrow precursor cells" refers to bone-marrow-derived endothelial precursors and/or circulating endothelial cell precursor cells.

The term "cancer cell" or "tumor cell" as used herein refers to a neoplastic cell. The term includes cancer cells that are benign as well as malignant. Neoplastic transformation is associated with phenotypic changes of the tumor cell relative to the cell type from which it is derived. The changes can include loss of contact inhibition, morphological changes, and aberrant growth. (see, Freshney, *Culture of Animal Cells a Manual of Basic Technique* (3rd edition, 1994).

"Inhibiting growth of a cancer" in the context of the invention refers to slowing growth and/or reducing the cancer cell burden of a patient that has cancer "Inhibiting growth of a cancer" thus includes killing cancer cells as well as slowing or arresting cancer cell growth.

As used herein, "therapeutic agent" refers to an agent that when administered to a patient suffering from a disease, in a therapeutically effective dose, will cure, or at least partially arrest the symptoms of the disease and complications associated with the disease.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

An indication that two polypeptides are substantially identical is that the first polypeptide is immunologically cross-reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used in this specification and the appended claims, the singular forms "a," "an," and "the" include plural referents unless the context clearly dictates otherwise.

I. Introduction

The invention relates to antibodies that bind to EphA3 with high affinity and typically, activate EphA3. The antibodies comprise variable regions with a high degree of amino acid sequence identity to human germ-line $V_H$ and $V_L$ sequences. In preferred embodiments, the CDRH3 of an antibody of the invention comprises the amino acid sequence $X_1GX_2YEX_3FDX_4$ (SEQ ID NO:38), wherein $X_1$ is S or G, $X_2$ is Y or V, $X_3$ is E or D, and $X_4$ is S, V, or I, with the proviso that the amino acid sequence is not SGYYEDFDS (SEQ ID NO:39). In some embodiments embodiment, CDRL3 of an antibody of the invention comprises the amino acid sequence $X_1X_2YX_3X_4YPYT$ (SEQ ID NO:56), wherein $X_1$ is G, V or A, $X_2$ is Q, R, or G, $X_3$ is A, S, or L, and $X_4$ is N or K.

Typically, the portion of the CDR3 excluding the BSD and the complete FR4 are comprised of human germ-line sequences. In some embodiments, the CDR3-FR4 sequence excluding the BSD differs from human germ-line sequences by not more than 2 amino acids on each chain. In some embodiments, the J-segment comprises a human germline J-segment. Human germline sequences can be determined, for example, through the publicly available international ImMunoGeneTics database (IMGT) and V-base (on the worldwide web at vbase.mrc-cpe.cam.ac.uk).

The human germline V-segment repertoire consists of 51 heavy chain V-regions, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, also Chothia et al., 1992, J Mol Biol 227:776-798; Tomlinson et al., 1995, EMBO J 14:4628-4638; and Williams et al., 1996, J Mol Biol 264:220-232).

Antibodies or antibodies fragments as described herein can be expressed in prokaryotic or eukaryotic microbial systems or in the cells of higher eukaryotes such as mammalian cells.

An antibody that is employed in the invention can be in any format. For example, in some embodiments, the antibody can be an including an constant region, e.g., a human constant region, e.g., an intact Ig, a Fab, Fab', $F(ab')_2$ or a fragment of an intact immunoglobulin, e.g., an scFv or Fv.

II. Heavy Chains

A heavy chain of an anti-EphA3 antibody of the invention comprises a heavy-chain V-region that comprises the following elements:

1) human heavy-chain V-segment sequences comprising FR1-CDR1-FR2-CDR2-FR3

2) a CDRH3 region comprising the amino acid sequence $X_1GX_2YEX_3FDX_4$ (SEQ ID NO:38), wherein $X_1$ is S or G, $X_2$ is Y or V, $X_3$ is E or D, and $X_4$ is S, V, or I, with the proviso that the amino acid sequence is not SGYYEDFDS (SEQ ID NO:39); and 3) a FR4 contributed by a human germ-line J-gene segment.

In some embodiment, the CDR3 comprises GGYYEDFDS (SEQ ID NO:43), SGYYEEFDS (SEQ ID NO:41), SGVYEDFDS (SEQ ID NO:44), SGYYEDFDV (SEQ ID NO:45), or SGYYEDFDI (SEQ ID NO:46).

The V-segment typically has at least 80% identity, or 85%, 90%, 95%, or greater identity to a human germline V-segment, e.g., a human VH1 subclass. Thus, in some embodiments, the V-segment is a human $V_H1$ 1-02 segment that at least 80%, 85%, 90%, 95%, 96%, 97%, 98%, or 99% or greater, identity to the germ-line segment VH1 1-02. In some embodiments, the V-segment differs by not more than 15 residues from VH1 1-02 and preferably not more than 10 residues.

In some embodiments, an antibody of the invention comprises a V-segment that has at least 90% identity, or at least 91%, 92% 93%, 94%, 95%, 96%, 97%, 98%, 99%, or 100% identity to the germ-line segment VH 1-02; or to one of the V-segments of the $V_H$ regions shown in FIG. 1.

The FR4 sequence of the antibodies of the invention is provided by a human JH1, JH3, JH4, JH5 or JH6 gene germline segment, or a sequence that has a high degree of amino-acid sequence identity, e.g., at least 90% or 95% identity, or differs at not more than 3, typically at not more than 2 amino acid residues in comparison to a human germline JH segment. In some embodiments, the J segment is from a human germline JH6 sequence and the FR4 has the sequence WGQGTTVTVSS (SEQ ID NO:47).

In some embodiments, the V-segment of the $V_H$ region has a CDR1 and/or CDR2 as shown in FIG. 1. For example, an antibody of the invention may have a CDR1 that has the sequence GYWMN (SEQ ID NO:48), TYWIS (SEQ ID NO:42), or SYWIN (SEQ ID NO:40). An antibody of the invention may have a CDR2 that has the sequence DIYPGS-GNTNYDEKFQG (SEQ ID NO:49), DIYPGSGNT-NYAQKFQG (SEQ ID NO:50), DIYPGSGNTNYAQEFRG (SEQ ID NO:51), DIYPGSGNTNYAQKFLG (SEQ ID NO:52), or DIYPGSGNTNYDEKFKR (SEQ ID NO:54). Thus, in some embodiments, an anti-EphA3 antibody of the invention may have a $V_H$ region CDR3 that has the sequence GGYYEDFDS (SEQ ID NO:43), SGYYEEFDS (SEQ ID NO:41), SGVYEDFDS (SEQ ID NO:44), SGYYEDFDV (SEQ ID NO:45), or SGYYEDFDI (SEQ ID NO:46), and a CDR1 sequence GYWMN (SEQ ID NO:48), TYWIS (SEQ ID NO:42), or SYWIN (SEQ ID NO:40) and a CDR2 DIYPGSGNTNYDEKFQG (SEQ ID NO:49), DIYPGS-GNTNYAQKFQG (SEQ ID NO:50), DIYPGSGNTNYAQE-FRG (SEQ ID NO:51), DIYPGSGNTNYAQKFLG (SEQ ID NO:52), or DIYPGSGNTNYDEKFKR (SEQ ID NO:54).

In some embodiments, an anti-EphA3 antibody of the invention may have a $V_H$ region CDR3 that has the sequence SGYYEDFDS (SEQ ID NO:39) and a CDR1 and/or a CDR2 of a VH region set forth in FIG. 1.

In some embodiments, a $V_H$ region V-segment of an antibody of the invention has a V-segment sequence shown in FIG. 1.

In typical embodiment, an antibody of the invention has a $V_H$ region sequence set forth in FIG. 1.

III. Light Chains

A light chain of an anti-EphA3 antibody of the invention comprises at light-chain V-region that comprises the following elements:

1) human light-chain V-segment sequences comprising FR1-CDR1-FR2-CDR2-FR3

2) a CDRL3 region that has the sequence CDR3 that comprises the sequence $X_1X_2YX_3X_4YPYT$ (SEQ ID NO:56), wherein $X_1$ is G, V or A; $X_2$ is Q, R, or G; $X_3$ is A, S, or L; and $X_4$ is N or K; and 3) a FR4 contributed by a human germ-line J-gene segment.

In some embodiments, the CDR3 has a sequence $X_1X_2YX_3X_4YPYT$ (SEQ ID NO:61), wherein $X_1$ is V, $X_2$ is Q, $X_3$ is A, and $X_4$ is N. In some embodiments the $V_L$ CDR3 is GQYANYPYT (SEQ ID NO:57), VQYAKYPYT (SEQ ID NO:58), AQYANYPYT (SEQ ID NO:59), VQYSNYPYT (SEQ ID NO:60), VQYANYPYT (SEQ ID NO:61), VGY-ANYPYT (SEQ ID NO:62), VRYANYPYT (SEQ ID NO:63), or VQYLNYPYT (SEQ ID NO:64).

The $V_L$ region comprises either a Vlambda or a Vkappa V-segment. An example of a Vkappa sequence that supports binding in combination with a complementary $V_H$-region is provided in FIG. 1.

The Vkappa segments may be of any subclass, e.g. and is often of the VκI sub-class. In some embodiments, the segments have at least 80% sequence identity to a human germline VκI e.g., at least 80% identity to the human germ-line VκI L15 sequence. In some embodiments, the Vic segment may differ by not more than 5 residues from VκI L15 In other embodiments, the $V_L$ region V-segment of an antibody of the invention has at least 85% identity, or at least 90%, 91%, 92%, 93%, 94%, 95%, 96%, 97%, 98%, 99%, or 100% identity to the human kappa V-segment sequence of a $V_L$ region shown in FIG. 1.

The FR4 sequence of the $V_L$ region of an antibody of the invention is provided by a human germline J segment, e.g. or a sequence that has a high degree of amino-acid sequence identity to a human germline J segment. In some embodiments, the J segment is a human germline Jκ2 sequence and the FR4 of the antibody has the sequence FGQGTKLEIK (SEQ ID NO:69).

In some embodiments, the V-segment of the $V_L$ region has a CDR1 and/or CDR2 as shown in FIG. 1. Thus, an antibody of the invention may have a CDR1 sequence of RASQGII-SYLA (SEQ ID NO:66), QASQDISTYLN (SEQ ID NO:70), RASQEISGYLG (SEQ ID NO:65), or RASQSISSYLA (SEQ ID NO:71) and/or a CDR2 sequence AASSLQS (SEQ ID NO:68), GASSLQS (SEQ ID NO:72), AASSLQR (SEQ ID NO:73), or AASTLDS (SEQ ID NO:67).

In particular embodiments, an anti-EphA3 antibody of the invention may have a $V_L$ region CDR1 and a CDR2 in a combination as shown in one of the V-segments of the $V_L$ regions set forth in FIG. 1 and a $V_L$ region CDR3 sequence that comprises GQYANYPYT (SEQ ID NO:57), VQYAKY-PYT (SEQ ID NO:58), AQYANYPYT (SEQ ID NO:59), VQYSNYPYT (SEQ ID NO:60), VQYANYPYT (SEQ ID NO:61), VGYANYPYT (SEQ ID NO:62), VRYANYPYT (SEQ ID NO:63), or VQYLNYPYT (SEQ ID NO:64). In some embodiments, such an anti-EphA3 antibody may comprise a $V_L$ region FR4 region that is FGQGTKLEIK (SEQ ID NO:69). Thus, a $V_L$ region of an anti-EphA3 antibody of the invention, can comprise, e.g., a CDR3 GQYANYPYT (SEQ ID NO:57), VQYAKYPYT (SEQ ID NO:58), AQYANYPYT (SEQ ID NO:59), VQYSNYPYT (SEQ ID NO:60), VQY-ANYPYT (SEQ ID NO:61), VGYANYPYT (SEQ ID NO:62), VRYANYPYT (SEQ ID NO:63), or VQYLNYPYT (SEQ ID NO:64); a CDR1 sequence RASQGIISYLA (SEQ ID NO:66), QASQDISTYLN (SEQ ID NO:70), RASQEIS-GYLG (SEQ ID NO:65), or RASQSISSYLA (SEQ ID NO:71); and a CDR2 sequence AASSLQS (SEQ ID NO:68), GASSLQS (SEQ ID NO:72), AASSLQR (SEQ ID NO:73), or AASTLDS (SEQ ID NO:67).

In some embodiments, a $V_L$ region V-segment of an antibody of the invention has a V-segment sequence shown in FIG. 1.

In typical embodiment, an antibody of the invention has a $V_L$ region sequence set forth in FIG. 1.

In some embodiments, an antibody of the invention comprises any one of the $V_L$ regions set forth in SEQ ID NOs:11-23 with any one of the $V_H$ regions set forth in SEQ ID NOs: 1-10.

IV. Preparation of EphA3 Antibodies

The affinity of an antibody may be assessed using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor.

Antibodies of the invention typically compete with mIIIA4 for binding to EphA3. The ability of an antibody described herein to block or compete with mIIIA4 for binding to EphA3 indicates that the antibody binds to the same epitope or to an epitope that is close to, e.g., overlapping, with the epitope that is bound by mIIIA4 for binding to EphA3. In other embodiments an antibody described herein, e.g., an antibody comprising a $V_H$ and $V_L$ region combination as shown in the table provided in FIG. 1, can be used as a reference antibody for assessing whether another antibody competes for binding to EphA3. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays, such as immunoblots.

In typical embodiments, the antibody is an activating antibody. An antibody may be tested to confirm that the antibody retains the activity of activating EphA3. The activity can be determined using any number of endpoints, including phosphorylation assays, or an indirect endpoint such as apoptosis.

Methods for the isolation of antibodies with V-region sequences close to human germ-line sequences have previously been described (US patent application publication nos. 20050255552 and 20060134098). Antibody libraries may be expressed in a suitable host cell including mammalian cells, yeast cells or prokaryotic cells. For expression in some cell systems, a signal peptide can be introduced at the N-terminus to direct secretion to the extracellular medium. Antibodies may be secreted from bacterial cells such as *E. coli* with or without a signal peptide. Methods for signal-less secretion of antibody fragments from *E. coli* are described in US patent application 20070020685.

To generate a EphA3-binding antibody, one of the $V_H$-regions of the invention, e.g., shown in FIG. 1, is combined with one of the $V_L$-regions of the invention, e.g., shown in FIG. 1, and expressed in any of a number of formats in a suitable expression system. Thus the antibody may be expressed as a scFv, Fab, Fab' (containing an immunoglobulin hinge sequence), $F(ab')_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems. Each of the $V_H$-regions described herein may be paired with each of the $V_L$ regions to generate an anti-EphA3 antibody.

Antibodies may be produced using any number of expression systems, including both prokaryotic and eukaryotic expression systems. In some embodiments, the expression system is a mammalian cell expression, such as a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a discistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention may be produced in any number of formats, including as a Fab, a Fab', a $F(ab')_2$, a scFv, or a dAB. An antibody of the invention can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA or IgM.

In some embodiments of the invention, the antibody $V_L$ region, e.g., a $V_L$ region set forth in FIG. 1, is combined with a human kappa constant region (e.g., SEQ ID NO:25) to form the complete light-chain.

In some embodiments of the invention, the $V_H$ region is combined a human gamma-1 constant region. Any suitable gamma-1 allotype can be chosen. Thus, in some embodiments, the antibody is an IgG having a constant region, e.g., SEQ ID NO:24, that has a $V_H$ selected from a $V_H$ region sequence set forth in FIG. 1. In some embodiments, the antibody has a $V_L$ selected from the $V_L$ region sequences set forth in FIG. 1. In particular embodiments, the antibody has a kappa constant region as set forth in SEQ ID NO:25, and a heavy chain constant region as set forth in SEQ ID NO:24, where the heavy and light chain variable regions comprise one of the following combinations from the sequences set forth in FIG. 1.

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227,2007).

In some embodiments, the antibodies of the invention are in the form of a Fab' or a $(Fab')_2$.

A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class.

An antibody that is employed in the invention can be in numerous formats. In some embodiments, the antibody can include an Fc region, e.g., a human Fc region. For example, such antibodies include IgG antibodies that bind EphA3 and that have an active isotype. In some embodiments, the antibody can be an active fragment (e.g., it can dimerize EphA3) or derivative of an antibody such as an Fab, Fab', $F(ab')_2$, Fv, scFv, or a single domain antibody ("dAb"). For example, in some embodiments, the antibody may be a $F(ab')_2$. Other exemplary embodiments of antibodies that can be employed in the invention include activating nanobodies or activating camellid antibodies. Such antibodies may additionally be recombinantly engineered by methods well known to persons of skill in the art. As noted above, such antibodies can be produced using known techniques. As appreciated by one of skill in the art, in some embodiments when an antibody is in a format that can be monovalent, e.g., an Fv or Fab format, the antibody may be employed as a multivalent antibody, such as a trivalent or tetravalent antibody. Methods of generating multivalent antibodies re known (see, e.g., King et al., *Cancer Res.* 54:6176-6185, 1994).

In many embodiments, an antibody for use in the invention has an Fc constant region that has an effector function, e.g., binds to an Fc receptor present on immune effector cells. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor), and the like. Such effector functions generally require the Fc region to be combined with a binding domain (e.g. an antibody variable domain) and can be assessed using known assays (see, e.g., the references cited hereinbelow.)

Anti-EphA3 antibodies that have an active isotype and are bound to Fc-receptors on effector cells, such as macrophages, monocytes, neutrophils and NK cells, can induce cell death by ADCC.

The Fc region can be from a naturally occurring IgG1, or other active isotypes, including IgG3, IgM, IgA, and IgE. "Active isotypes" include antibodies where the Fc region comprises modifications to increase binding to the Fc receptor or otherwise improve the potency of the antibody. Such an Fc constant region may comprise modifications, such as mutations, changes to the level of glycosylation and the like, that increase binding to the Fc receptor. There are many methods of modifying Fc regions that are known in the art. For example, U.S. Patent Application Publication No. 20060039904 describes variants of Fc receptors that have enhanced effector function, including modified binding affinity to one or more Fc ligands (e.g., FcγR, C1q). Additionally, such Fc variants have altered antibody-dependent cell-mediated cytotoxicity (ADCC) and/or complement dependent cytotoxicity (CDC) activity. Other Fc variants include those disclosed by Ghetie et al., *Nat Biotech.* 15:637-40, 1997; Duncan et al, *Nature* 332:563-564, 1988; Lund et al., *J. Immunol* 147:2657-2662, 1991; Lund et al, *Mol Immunol* 29:53-59, 1992; Alegre et al, *Transplantation* 57:1537-1543, 1994; Hutchins et al., *Proc Natl. Acad Sci USA* 92:11980-11984, 1995; Jefferis et al, *Immunol Lett.* 44:111-117, 1995; Lund et al., *FASEB J*9:115-119, 1995; Jefferis et al, *Immunol Lett* 54:101-104, 1996; Lund et al, *J Immunol* 157:4963-4969, 1996; Armour et al., *Eur J Immunol* 29:2613-2624, 1999; Idusogie et al, *J Immunol* 164:4178-4184, 200; Reddy et al, *J Immunol* 164:1925-1933, 2000; Xu et al., *Cell Immunol* 200:16-26, 2000; Idusogie et al, *J Immunol* 166:2571-2575, 2001; Shields et al., *J Biol Chem* 276:6591-6604, 2001; Jefferis et al, *Immunol Lett* 82:57-65. 2002; Presta et al., *Biochem Soc Trans* 30:487-490, 2002; Lazar et al., *Proc. Natl. Acad. Sci. USA* 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091; and PCT Publications WO 94/2935; WO 99/58572; WO 00/42072; WO 02/060919, and WO 04/029207.

Glycosylation is a form of post-translational modification by which carbohydrates (sugars) are enzymatically linked to macromolecules to produce glycans. In the context of the present invention, carbohydrates are typically attached to antibody Fc region via one or more N-linkages (through a nitrogen of asparagine or arginine side chains); however, O-linkages (via hydroxy oxygen of serine, threonine, tyrosine, hydroxylysine, or hydroxyproline side chains) are also possible. Generally, IgG antibodies have a conserved N-linked glycosylation site in the CH2 domain at residue Asn297, while some classes and subclasses also have O-linked sugars, often in the hinge region, e.g. IgD and IgA of some species. The sugars are typically complex, high-mannose, branched sugars; in the case of N-linkages, the sugar that attaches directly to the amino acid sidechain nitrogen is typically N-acetyl glucosamine.

In some embodiments, the glycosylation of Fc regions may be modified. For example, a modification may be aglycosylation, for example, by altering one or more sites of glycosylation within the antibody sequence. Such an approach is described in further detail in U.S. Pat. Nos. 5,714,350 and 6,350,861. An Fc region can also be made that has an altered type of glycosylation, such as a hypofucosylated Fc variant having reduced amounts of fucosyl residues, or an afucosylated Fc variant lacking fucosyl residues, or an Fc variant having increased bisecting GlcNAc structures. Such carbohydrate modifications can be accomplished by, for example, expressing the antibody in a host cell with altered glycosylation machinery. Cells with altered glycosylation machinery, including rat myeloma cells as well as yeast and plants, have been described in the art and can be used as host cells in which to express recombinant antibodies of the invention to thereby produce an antibody with altered glycosylation.

Umana et al, *Nat. Biotechnol* 17:176-180, 1999, which describes bisected GlcNac resulting in 10 times ADCC. Umana notes that such bisected molecules result in less fucosylation. Davies, et al., *Biotechnol. Bioeng.* 74:288-294, 2001 describe CHO cells with inserted enzyme β1-4-N-acetylglucosaminyltransferase III (GnTIII) (which causes the bisected GlcNac structure) resulting in increased ADCC of anti-CD20 antibodies. (Umana) U.S. Pat. No. 6,602,684 describes cells engineered to produce bisecting GlcNac glycoproteins.

Examples of methods to reduce fucosylation of an antibody preparation are provided in Shields et al, *J Biol Chem* 277:26733-26740, 2002, which describes CHO cells (Lec13) deficient in fucosylation to produce IgG1 and further describes that binding of the fucose-deficient IgG1 to human FcgammaRIIIA was improved up to 50-fold and increased ADCC. In addition, Shinkawa et al., *J Biol Chem* 278:3466-3473, 2003; compare IgG produced in YB2/0 and CHO cells. The YB2/0 cells have decreased fucosylation and increased bisecting GlcNac content. Niwa et al., *Clinc. Cancer Res.* 1-:6248-6255, 2004 compare anti-CD20 antibodies with antibodies made in YB2/0 cells (low fucosylation) and observed enhanced ADCC in the latter. Examples of techniques to produce afucosylated antibodies are provided, for example, in Kanda et al, *Glycobiology* 17:104-118, 2006. U.S. Pat. No. 6,946,292 (Kanda) describes fucosyltransferase knock-out cells to produce afucosylated antibodies. U.S. Pat. No. 7,214,775 and WO 00/61739 describe antibody preparations in which 100% of the antibodies are afucosylated.

Other techniques to modify glycosyation are also known. See, for example, U.S. Patent Application Publication Nos. 20070248600; 20070178551 (GlycoFi technology methods employing engineered lower eukaryotic cells (yeast) to produce "human" glycosylation structures); 20080060092 (Biolex technology methods employing engineered plants to produce "human" glycosylation structures); 20060253928 (which also described engineering of plants to produce "human" antibodies.

Additional techniques for reducing fucose include ProBioGen technology (von Horsten et al., *Glycobiology*, (advance access publication Jul. 23, 2010); Potelligent™ technology (Biowa, Inc. Princeton, N.J.); and GlycoMAb™ glycosylation engineering technology (GLYCART biotechnology AG, Zurich, Switzerland).

The N-linked oligosaccharide content of an antibody can be analyzed by methods known in the art. The following is an example of such a method: Antibodies are subjected to digestion with the enzyme N-glycosidase F (Roche; TaKaRa). Released carbohydrates are analyzed by matrix assisted laser desorption/ionization time-of-flight mass spectrometry (MALDI-TOF MS) with positive ion mode (Papac et al., *Glycobiol.* 8: 445-454, 1998). Monosaccharide composition is then characterized by modified high-performance anion exchange chromatography (HPAEC) (Shinkawa et al., *J. Biol. Chem.* 278: 3466-3473, 2003).

In some embodiments of the invention, the antibody is additionally engineered to reduce immunogenicity, e.g., so that the antibody is suitable for repeat administration. Methods for generating antibodies with reduced immunogenicity include humanization and humaneering procedures and modification techniques such as de-immunization, in which an antibody is further engineered, e.g., in one or more framework regions, to remove T cell epitopes.

In some embodiments, antibodies are employed in a form that can activate EphA3 present on the surface of EphA3-expressing cells, e.g., vasculogenic bone marrow precursor cells, or that can kill such cells by ADCC. Thus, in some embodiments an antibody is dimeric. In other embodiments, the antibody may be in a monomeric form that has an active isotype. In some embodiments the antibody is in a multivalent form, e.g., a trivalent or tetravalent form, that can cross-link EphA3.

V. Administration of Anti-EphA3 Antibodies for the Treatment of Diseases in which EphA3 is a Target.

The invention also provides methods of treating a patient that has a disease in which it is desirable to kill EphA3-expressing cells. In some embodiments, such a disease may be a neoplastic disease. Accordingly, in one aspect, the invention provides a method of treating a neoplastic disease using an antibody of the invention where the method comprises administering an anti-EphA3 antibody of the invention to a patient (that has a tumor) to inhibit tumor growth. Tumors that can be treated include tumors of the breast, lung, colon, stomach, liver, kidney, ovary, esophagus, and prostate, and the others. A solid tumor treated with an antibody of the invention can therefore be a breast carcinoma, lung carcinoma, prostate carcinoma, gastric carcinoma, esophageal carcinoma, colorectal carcinoma, liver carcinoma, ovarian carcinoma, vulval carcinoma, kidney carcinoma, cervical carcinoma, endometrial carcinoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreatic carcinoma, retinoblastoma, astrocytoma, glioblastoma, Schwannoma, oligodendroglioma, medulloblastoma, neuroblastomas, sarcomas include fibrosarcomas, rhabdomyosarcoma, osteogenic sarcoma, leiomyosarcoma, urinary tract carcinoma, thyroid carcinoma, and Wilm's tumor. Abnormal vascular proliferation associated with phakomatoses, and edema (such as that associated with brain tumors) can also be treated with an antibody of the invention.

In some embodiments, the anti-EphA3 antibody is administered to a patient that expresses EphA3 on the surface of the tumor cells. In some embodiments, the anti-EphA3 is administered to a patient that expresses EphA3 on the endothelium of blood vessels in the tumor. In some embodiments, the patient may express EphA3 on both the tumor cell surface and the endothelium. In some embodiments, the antibody is in a format as described, e.g., in WO/2008/112192.

In some embodiments, a non-neoplastic condition is treated using an antibody of the invention. The non-neoplastic condition is selected from the group consisting of undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osier-Weber syndrome, pyogenic granuloma retrolental fibroplasias, scleroderma, trachoma, vascular adhesions, synovitis, dermatitis, preeclampsia, ascites, pericardial effusion, and pleural effusion.

In some embodiments, an antibody of the invention is administered to a patient suffering from a myeloproliferative disorder. In some embodiments, the myeloproliferative disorder is acute myeloid leukemia, chronic myeloid leukemia, myelodysplastic syndrome, polycythemia vera (PV), essential thrombocythemia (ET), or idiopathic myelofibrosis (IM). In some embodiments, an anti-EphA3 antibody of the invention can be used in combination with one or more additional therapeutic agents to treat a patient that has chronic myeloid leukemia where leukemic stem cells from the patient express EphA3. Such therapeutic agents include various chemotherapeutic agents and imatinib mesylate (GLEEVEC®).

The antibody may be administered alone, or in combination with other therapies to treat the disease of interest. In some embodiments, the anti-EphA3 antibody is administered in combination with a Bv8 antagonist, e.g., a Bv8 antibody antagonist. Bv8 antagonists are known (see, e.g., WO 2009039337 and the references relating to Bv8 antagonists cited therein). For example, Bv8 antagonists include, antibodies and antibody fragments specifically binding to a native sequence Bv8 polypeptide, or a native sequence Bv8 receptor (PKR-I/EG-VEGFR1 or PKR-2/EG-VEGFR2) polypeptide. In some embodiments, a patient may also be treated with additional therapeutic agents, including a VEGF antagonist, e.g., an anti-VEGF antibody antagonist, as well as other therapeutic agents, examples of which are additionally described below.

In some embodiments, the anti-EphA3 antibody is administered to a patient that has previously been treated with a VEGF antagonist, e.g., an anti-VEGF antibody antagonist. In some embodiments, the tumor may be refractory to treatment with a VEGF antagonist. In some embodiments, the anti-EphA3 antibody is administered to a patient that has an early stage tumor, e.g., a Stage I, Stage II, or Stage III tumor.

A patient that is considered to be refractory to treatment with a VEGF antagonist, e.g., a VEGF antibody antagonist, or has a tumor that is refractory to treatment with a VEGF antagonist as used herein refers to a patient who responds to therapy, but suffer from side effects, develops resistance, does not respond to the therapy, does not respond satisfactorily to the therapy, etc. Thus, in such patients, or the tumors from such patients, the number of tumor cells has not been significantly reduced, or has increased, or tumor size has not been significantly reduced, or has increased, or there is not further reduction in size or in number of cancer cells. The determination that the patient is refractory to treatment can be made either in vivo or in vitro by any method known in the art for assaying the effectiveness of treatment on cancer cells. Similarly, a patient who has a non-neoplastic condition that is refractory to treatment with a VEGF antagonist, e.g., a VEGF antibody, in the context of this invention refers to a patient who does not respond satisfactorily to treatment with the VEGF antagonist, for example, the patient suffers side effects, develops resistance, or does not exhibit reduction in therapeutic indicators for the condition.

The methods of the invention comprise administering an anti-EphA3 antibody as a pharmaceutical composition to a patient in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005.

The anti-EphA3 antibody is provided in a solution suitable for injection into the patient such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient, e.g., a patient that has a tumor or non-neoplastic condition, in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of the disease in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of anti-EphA3 antibody to effectively treat the patient.

The antibody can be administered by injection or infusion through any suitable route including but not limited to intravenous, sub-cutaneous, intramuscular or intraperitoneal routes. In some embodiments, the antibody may be administered by insufflation. In an exemplary embodiment, the antibody may be stored at 10 mg/ml in sterile isotonic aqueous saline solution for injection at 4° C. and is diluted in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. Preferably the dose is in the range 1-10 mg/kg or approximately 50 mg-1000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months. In other embodiments, the antibody is administered approximately once per month.

A $V_H$ region and/or $V_L$ region of the invention may also be used for diagnostic purposes. For example, the $V_H$ and/or $V_L$ region may be used for clinical analysis, such as detection of EphA3 levels on cells from a patient. A $V_H$ or $V_L$ region of the invention may also be used, e.g., to produce anti-Id antibodies.

EXAMPLES

Methodology

Sub-Cloning of Murine V-regions

The V-region DNA from murine monoclonal mIIIA4 were provided by Dr. Martin Lackmann (Department of Biochemistry and Molecular Biology, Monash University, Victoria, Australia). PCR was used to amplify the V-genes of the V-heavy and V-kappa regions and incorporate restriction enzyme sites suitable for cloning into the desired vectors. V-regions were cloned as Fab fragments and expressed in *E. coli*. This Fab was tested for EphA3-Fc antigen binding and is referred to as reference sequence FA4 in these examples.

Antibody Purification

Fab fragments were expressed by secretion from *E. coli*. Cells were grown in 2xYT medium to an $OD_{600}$ of 0.6. Expression was induced using IPTG for 3 hours at 33° C. Assembled Fabs were obtained from periplasmic fractions and purified by affinity chromatography using Streptococcal Protein G (HiTrap Protein G HP columns; GE Healthcare) according to standard methods. Fabs were eluted in pH 2.0 buffer, immediately adjusted to pH 7.0 and dialyzed against PBS pH 7.4 (PBS is without calcium and magnesium).

ELISA

Typically 50 ng of antigen was bound to a 96 well microtiter plate by overnight incubation at 4° C. The plate was blocked with a solution of 5% milk in PBS for one hour at 33° C. Induced medium (50 μl) from *E. coli* expressing each Humaneered Fab or optimized reference Fab FA106 was added to each well. After a one hour incubation at 33° C., the plate was rinsed three times with PBS+0.1% Tween 20 (PBST), 50 μl of anti-human-kappa chain HRP conjugate (Sigma; diluted to 0.1 ng/ml in PBST) was added to each well, and the plate was incubated for 40 min at 33° C. The plate was washed three times with PBST and once with PBS. The substrate 3,3',5,5' tetramethylbenzidine (TMB), 100 μl (Sigma), was added to each well and the plate was incubated for ~5 min at room temperature. To stop the reaction, 100 μl of 0.2 N $H_2SO_4$ was added to each well. The reactions were read at 450 nm by spectrophotometry.

For detection of binding to Eph family members, recombinant human Eph extracellular (ec) domains were obtained from R&D Systems Inc: EphA1-Fc fusion protein, EphA2 ec domain, EphA5 ec domain, EphB4 ec domain and EphB6-Fc fusion protein. ELISA wells were coated with 100 ng of Eph protein for 1 hr at 37° C. After washing once with PBST, wells were blocked with 5% milk in PBST at 37° C. for one hour. Wells were washed once and a two fold dilution series of candidate humaneered antibody added to each set of coated Eph proteins. After one hour, the wells were washed three times in PBST and 50 μl of anti-human-kappa chain HRP conjugate (Sigma; diluted to 0.1 ng/ml in PBST) was added to each well. The plate was incubated for 45 minutes, washed 3 times with PBST, washed one with PBS and 100 μl of TMB added to each well. The reaction was stopped by addition of 0.2N $H_2SO_4$ and binding measured by absorbance at 450 nm.

Colony Lift Binding Assay (CLBA)

Screening of Humaneered libraries of Fab fragments was carried out as described (U.S patent Application Publication Nos. 20050255552 and 20060134098) using antigen coated nitrocellulose filters.

Affinity Measurements

The binding kinetics of Fab fragments were analyzed using surface plasmon resonance analysis (spr; Biacore T100) at Biosensor Tools Inc. Affinities were calculated from the determined association and dissociation constants at three different Fab concentrations.

Construction of IgGs

Chimeric IIIA4 IgG was constructed to contain human IgG1 constant regions and variable regions from the original mouse IIIA4 antibody. PCR was used to amplify the heavy and light chains from mouse IIIA4 DNA provided by Martin Lackmann and also to incorporate restriction sites for cloning. The heavy chain variable region was cloned into a vector expressing the full IgG1 heavy chain expressed from a CMV promoter located downstream of a UCOE sequence. The plasmid contains the Neo gene for selection in mammalian cells and the Amp gene for plasmid production in *E. coli*. Similarly, the light chain variable region was cloned into a vector expressing the human kappa light chain constant region, expressed from a CMV promoter downstream of a UCOE sequence. The plasmid contains a gene for hygromycin selection in mammalian cells and the Amp gene for production in *E. coli*. Engineered antibody IgG heavy and light chain vectors were constructed similarly except the DNA for the variable regions was obtained from *E. coli* expression vectors described above and the heavy chain expression vector contained the puromycin resistance gene instead of neomycin. Humaneered antibody IgG and chimeric IIIA4 IgG were expressed in a modified CHO cell line by cotransfection of the heavy and light chain constructs using Fugene 6 reagent (Promega).

Flow Cytometry

Typically, $3\times10^6$ cells of SKmel28, LnCAP and B16-F10 were collected by centrifugation at 3000 rpm for 3 minutes. Media were removed and the cells blocked with 2% BSA in PBS for 30 minutes at 4° C. followed by a second block with 10 μg/ml rat IgG for 30 minutes at 4° C. Cells were pelleted, re-suspended in 1.5 ml PBS and divided into 500 μl aliquots. Each aliquot was probed separately with 5 μg/ml of control IgG, humaneered IgG or chimeric IIIA4 IgG for 45 minutes at 4° C. The samples were washed once in PBS and anti-human IgG-phycoerythrin-conjugate was added. After 45 minutes, cells were washed once, re-suspended in PBS and analyzed by flow cytometry using a FACS Caliber flow cytometery. Propidium iodide was added just prior to analysis to exclude dead cells.

Example 1

Identification of Engineered Human Anti-EphA3 Antibodies

Murine and Reference V-Region Amino Acid Sequences

Murine (mIIIA4) and a reference (FA4) V-region sequences are shown below. CDR sequences are underlined.

mIIIA4 and FA4 Vh (SEQ ID NO: 78):
EVKLEESGAELVKPGSSVKLSCKASGYNFTSYWINWVRLRPGQGLEWIGD -continued

IYPGSGNTNYDEKFKRKATLTVDTSSSTAYMQLSSLASEDSALYYCTRSG

YYEDFDSWGQGTTLIVSS mIIIA4 and FA4 Vk (SEQ ID NO: 79):
DIVLTQTPSSLSASLEERVSLTCRASQEISGYLGWLQQKPDGTIKRLIYA

ASTLDSGVPKKFSGNRSGSEYSLTISSLESEDFADYYCVQYANYPYTFGG

GTKLEIK

The Fab FA4 has intact murine V-regions from mIIIA4 fused with human constant regions and was purified from *E. coli*. A dilution ELISA of Fab fragments binding to the antigen produced binding curves that were dependent on antibody concentration.

In addition to the reference Fab (FA4), an optimized reference Fab (FA106) was constructed. Several framework amino acid residues in FA4 were changed to human germ-line in the optimized reference Fab FA106. The V-region sequences of the optimized reference Fab are provided below. The residues altered to human germ-line are shown as bold font. CDR sequences are underlined.

FA106 Vh (SEQ ID NO: 80):
EVKLEESGAELVKPGSSVKLSCKASGYNFTSYWINWVRLRPGQGLEWIGD

IYPGSGNTNYDEKFKRKATLTVDTSSSTAYMQLSSLASEDTAVYYCARSG

YYEDFDSWGQGTTVTVSS

FA106 Vk (SEQ ID NO: 81):
DIVLTQTPSSLSASLEERVSLTCRASQEISGYLGWLQQKPDGTIKRLIYA

ASTLDSGVPKKFSGNRSGSEYSLTISSLESEDFATYYCVQYANYPYTFGQ

GTKLEIK

Library Construction and V-Region Cassettes

Epitope-focused libraries were constructed from a human V-segment library sequences linked to the unique CDR3-FR4 region containing the BSD and human germ-line J-segment sequences. The "full-length" Vh (Vh1 and Vh5) and Vk (VkI) libraries were used as a base for construction of "cassette" libraries in which only part of the murine V-segment is initially replaced by a library of human sequences. Several types of cassettes "libraries" were constructed for both the Vh and Vk chains. Cassettes for the V-heavy and V-kappa chains were made by bridge PCR with overlapping common sequences within the framework 2 region. In this way "front-end" human cassette libraries were constructed for both human Vh1 and Vh5 subclasses and a "middle" human cassette library was constructed for human Vh1. "Front end" and "middle" cassette libraries were constructed for the Vk I subclass.

Additionally, a cassette library consisting of Vh CDR2-FR3 was constructed. A schematic is shown in FIG. 2. The first four residues (boxed) of the reference CDR2 were encoded by the 5' PCR primer. Also, the underlined amino acid residues in the mIIIA4 CDR2 and the human germ-line Vh1-58 CDR2 were varied in pair-wise combination in the forward primer (shown by the amino acid residues above and below the line). The 3' PCR primer is complementary to human germ-line Vh1 FR3. The primers were used to amplify and append a Hu Vh1 FR3 library (derived from spleen mRNA) to the engineered CDR2 library. Consecutive bridge PCR reactions were used to attach "front end" and CDR3-FR4 cassettes to construct a functional V-region.

Human Vh or Vk cassettes that supported binding to the antigen were identified by colony-lift binding assay and a rank order was determined according to affinity by ELISA. V-heavy screening identified "front-end", "middle" and CDR2/FR3 cassettes that supported EphA3-Fc recombinant fusion protein antigen binding. V-kappa screening identified "front-end" and "middle" cassettes that supported antigen binding. The functional cassettes for each chain were recombined to construct a fully engineered, high affinity Fab that bound antigen.

After the identification of a pool of high affinity, engineered Fabs, CDR3 affinity maturation libraries were built. The common CDR3 BSD sequences of a panel of engineered Fab clones were mutated using degenerate PCR primers to generate libraries. These mutagenic libraries were screened using colony lift binding and ELISA assays. The selected Fabs were ranked for affinity with ELISA. Mutations that supported similar or improved affinity for antigen when compared to the FA106 Fab were identified. The heavy chain and light chain CDR3 mutations that support or improve antigen binding help to define the BSD region for each CDR.

Reference and Humaneered Fab Sequence Alignment

Aligned V-segments of murine reference and two engineered Fabs amino acid sequences were compared with the closest single human germ-line V-gene, Vh1-02 or VkI L15. The FR4 for the humaneered Fab Vh-regions is from human germ-line JH6 and has the sequence WGQGTTVTVSS (SEQ ID NO:47). The FR4 for the humaneered Fab Vk-regions is from human germ-line Jk2 and has the sequence FGOGTKLEIK (SEQ ID NO:69).

Each of the Vh-regions and Vk-regions of the engineered Fabs have a high homology to human germ-line amino acid sequence. Exemplary homologies are shown in Table 1.

TABLE 1

Percentage identity to human germ-line sequence for two engineered V-regions: all percentages represent identity to a single human germ-line sequence across the V-region and exclude the CDR3 BSD sequences

| Humaneered Fab | Vh versus Vh1-02 | Vk versus VkI L15 |
|---|---|---|
| 1 | 93% | 95% |
| 2 | 91% | 95% |

Example 2

Binding Kinetics of Engineered Antibodies

Engineered Fabs were isolated from colony-lift binding assays and affinity confirmed by antigen-binding ELISA. Engineered Fab clones with strong positive signals in antigen-binding ELISA were purified and further characterized by kinetic comparison with the optimized reference Fab FA106.

Binding kinetics of two engineered Fabs and reference Fab FA106 were analyzed using a Biacore. The three Fabs were diluted from the starting concentration of 500 nM to 100 nM and further tested in a three-fold dilution series using PBS, pH 7.4 with 0.005% Tween-20 and 0.1 mg/ml BSA. Each of the five concentrations was tested three times over the three different density surfaces. Assays were run at 25° C. The response data from each surface were fit to a 1:1 interaction model. Calculated association and dissociation constants are shown in Table 2. Kinetic analysis of engineered Fab clones 1 and 2 and the reference clone FA106 all showed low nanomolar affinities for the antigen.

TABLE 2

Humaneered Fab Binding constants determined at 25 degrees C.

| | $k_a$ ($M^{-1}s^{-1}$) | $k_d$ ($s^{-1}$) | $K_D$ (nM) |
|---|---|---|---|
| Low | 1.83E6 | 0.00193 | 1.052 |
| medium | 1.01E6 | 0.001513 | 1.5 |
| high | 1.60E6 | 0.00186 | 1.16 |
| Humaneered Fab 1 avg | 1.4(4)E6 | 1.7(2)E−3 | 1.2(2) |
| low | 4.10E6 | 0.0058 | 1.4 |
| medium | 6.11E5 | 0.00178 | 2.91 |
| high | 1.67E6 | 0.00345 | 2.06 |
| FA106 avg | 2(1)E6 | 3(2)E−3 | 2.1(8) |
| low | 5.14E5 | 0.00332 | 6.45 |
| medium | 6.50E5 | 0.00399 | 6.16 |
| high | 3.52E5 | 0.00279 | 7.92 |
| Humaneered Fab 2 avg | 5(1)E5 | 3.3(6)E−3 | 6.8(9) |

The number in parentheses represents the standard error in the last reported digit based on the data from the three different density surfaces. The terms "low", "medium", and "high" in the left column refer to chip densities.

Humaneered Fab1 was expressed as an IgG in mammalian cells and purified from culture supernatant. Fab fragment was generated by papain digestion for analysis of monovalant binding affinity. Binding of Fab to human and mouse EphA3-Fc was measured on a Biacore 3000 using biotinylated EphA3 variants captured on a Streptavidin chip. Fab was diluted in HBSP running buffer from 50 nM to 0.62 nM with 3× dilutions. Results were double blanked with an empty reference cell and multiple HBSP buffer injections. Global fit analysis of the Biacore data was carried out assuming a 1:1 interaction. The binding kinetics parameters are shown in Table 3. The data show that Humaneered Fab1 produced from mammalian cells binds with high affinity to both human and murine EphA3.

TABLE 3

Engineered Fab 1 Binds Human and Mouse EphA3 with Comparable Affinity

| Analyte | $k_a$ (1/Ms) | $k_d$ (1/s) | $K_D$ (pM) |
|---|---|---|---|
| Human EphA3-Fc | $2.2 \times 10^6$ | $2.0 \times 10^{-3}$ | 930 |
| Mouse EphA3-Fc | $2.3 \times 10^6$ | $1.8 \times 10^{-3}$ | 800 |

Binding of Fab 1 to immobilized mouse and human EphA3-Fc fusion proteins was analyzed by surface plasmon resonance analysis using a Biacore 3000 instrument and global fit analysis.
$k_a$ = association constant;
$k_d$ = dissociation constant;
$K_D$ = overall affinity.

Binding and Specificity

Figure 3:
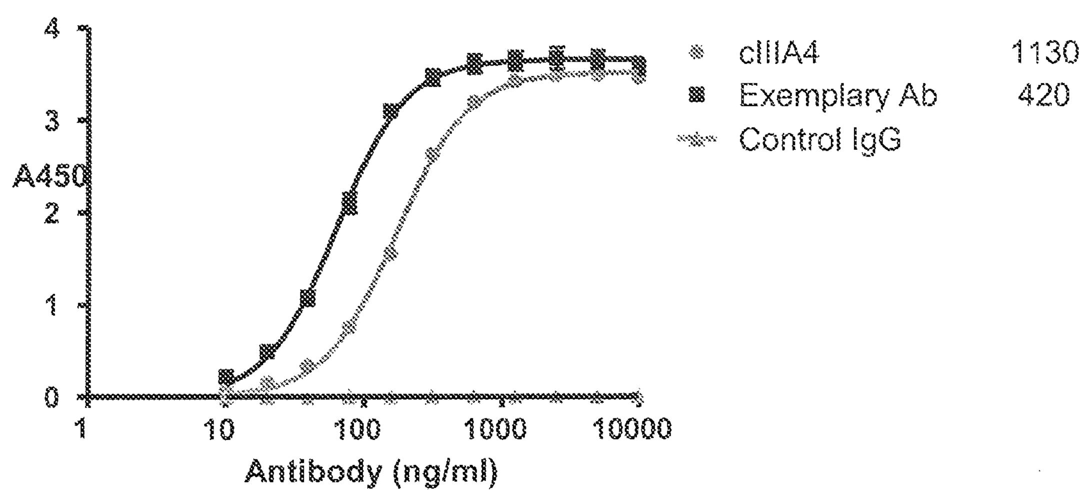
FIG. 3 shows results of an antigen binding ELISA with anti-EphA3 IgGs. ELISA plates coated with EphA3-Fc were treated with chimeric IIIA4 (circles), an exemplary engineered antibody of the invention (squares) or a control IgG (triangles) and probed for binding with an anti-human kappa chain HRP conjugate.

A full-length antibody (IgG1κ) was constructed, expressed from CHO cells and purified by Protein A affinity chromatography. ELISA plates were coated with EphA3-Fc and binding of cIIIA4 IgG, an exemplary engineered IgG, and a control IgG1 were compared (FIG. 3). The $EC_{50}$ in this assay was approximately three-fold lower for the engineered IgG than for the original chimeric antibody.

EphA3 is a member of the Eph receptor family which binds Ephrin ligands. The most homologous members of the family are the EphA receptors whose extracellular domains vary between 39% and 62% sequence identity to EphA3.

Figure 4:
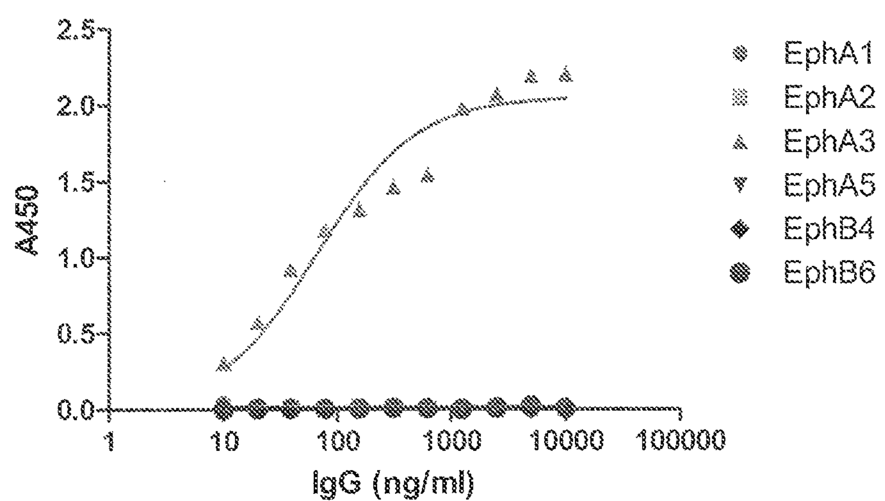
FIG. 4 shows the specificity of an engineered antibody of the invention for EphA3. Various Eph proteins were coated onto an ELISA plate, treated with engineered antibody and probed for binding with an anti-human kappa chain HRP conjugate.

To confirm the specificity of the exemplary engineered IgG, binding was assessed against three EphA proteins and two more distantly related EphB proteins (see FIG. 4). EphA5 homology to EphA3 is 61% and represents one of the most homologous family members to EphA3. The engineered antibody bound EphA3 specifically; binding was not observed to EphA1, EphA2 or EphA5. There was also no detectable binding to either of two EphB receptors tested (EphB4 and EphB6).

Figure 5:
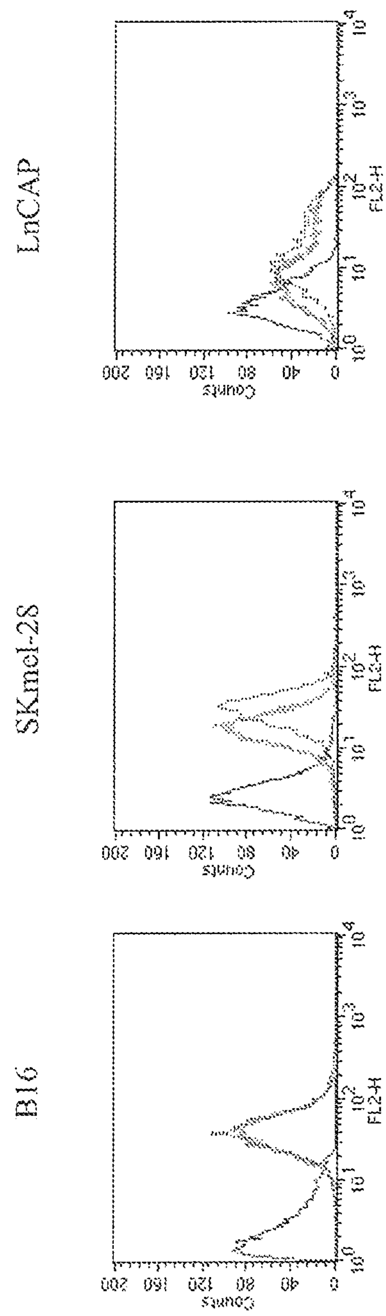
FIG. 5 shows data from flow cytometric analysis of three cell lines in an experiment evaluated the ability of an exemplary engineered anti-EphA3 antibody of the invention to bind to cell surface expressed EphA3. B16, SKmel28, and LnCAP cells were blocked with 2% BSA and rat IgG and probed with engineered anti-EphA3 IgG, chimeric IIIA4 IgG or an isotype control IgG. Bound antibody was detected by an anti-human IgG Phycoerythrin conjugate using a Facs Caliber flow cytometry (BD). Dead cells were excluded by propidium iodide staining For each graph, the control antibody profile is the left-most curve shown in the graph.

The exemplary engineered antibody was also tested for binding to EphA3 expressed on the surface of live cells. Three tumor cell lines known to express EphA3 were used: a mouse melanoma (B 16), a human melanoma (SKmel28), and a prostate cancer line (LnCAP). Live cells were probed with the engineered IgG, chimeric IIIA4 or a control antibody. Bound antibody was detected using flow cytometry by an anti-human IgG phycoerythrin conjugate (FIG. 5). Strong binding was observed for both the engineered IgG and Chimeric IIIA4 to B16 and SKmel28 cells. Both IgGs also bound LnCAP.

Example 3

Evaluation of the Ability of Fab and F(ab')2 Fragments to Induce Apoptosis

Fab fragments were generated by papain digestion of an exemplary engineered IgG1 antibody of the invention (Ab1) or control human IgG1 antibody. One mg of antibody was incubated with 0.01 mg of papain (Roche #10108014001) in 100 mM Sodium Acetate pH 5.0 at 37° C. for 18 h. F(ab')2 was produced by pepsin digestion. Five mg of IgG was incubated with 250 μl immobilized pepsin agarose slurry (Pierce #20343) at 37° C. for 18 h in 100 mM Sodium Acetate pH 4.0. Upon cleavage, both digests were incubated with protein A resin for 30 minutes to remove Fc fragments and the supernatants were collected. Fab and $F(ab')_2$ fragments were dialyzed into 50 mM Na Succinate pH 6.0, 145 mM NaCl and 0.05% Tween 80.

To evaluate the ability of Fab and $F(ab')_2$ fragments of Ab1 to induce apoptosis in primary cells isolated from leukemia patients, cells were seeded at $2\times10^5$ cells/well in 96-well "U"-bottom plates in 0.1 ml culture medium (RPMI 1640 with 10% fetal bovine serum). Antibody or antibody fragment was added to final concentrations of 10 μg/ml and the plates were incubated at 37° C. and 5% carbon dioxide in a tissue-culture incubator for 24 hours. As a positive control for apoptosis induction, separate cell samples were incubated with camptothecin (10 μM; Calbiochem). At the end of the incubation, cells were harvested and washed by centrifugation at 1000 rpm for 5 min followed by incubation in 0.1 ml buffer containing 10 μl FITC-conjugated Annexin V (BD Pharmingen) for 30 minutes on ice. Cells were washed once by centrifugation and resuspended in flow cytometry buffer containing propidium iodide (Sigma) diluted 1:1000 Annexin V-staining cells undergoing apoptosis were identified by flow cytometry.

TABLE 4

Induction of apoptosis by Ab1 antibody and antibody fragments

| Treatment | Apoptosis (%) Experiment 1 | Apoptosis (%) Experiment 2 |
|---|---|---|
| Engineered Ab1 IgG | 82.0 | 85 |
| hIgG1 control | 1.8 | — |
| $(Fab')_2$ | 16.3 | 23 |
| $(Fab')_2$ control | 1.3 | 0.8 |
| Engineered Ab1 Fab | 1.1 | 1.1 |
| Fab control | 0 | 0 |
| Camptothecin | 91.0 | 97.0 |

The results in Table 4 show that an exemplary antibody (Ab1) $F(ab')_2$ fragment induced direct induction of apoptosis in primary leukemia cells expressing EphA3. Approximately 20% of the target cells were killed within 24 hours using 10 μg/ml Ab1 $F(ab')_2$. In contrast, the monovalent Fab fragment was not able to induce detectable levels of apoptosis, indicating that dimerization of EphA3 is necessary and sufficient to induce significant levels of apoptosis in these cells and Fc effector functions are not required for apoptosis induction.

Example 4

Evaluation of an Afucosylated Antibody

Antibody 1 was produced in two glycosylation forms by expression in different CHO cell lines. One form (fucosylated Antibody 1) has glycosylation patterns typical of an IgG1κ (f-allotype) therapeutic antibody including α 1,6 fucose. The other form (designated afucosylated Antibody 1) is produced in a CHO cell line containing a homozygous deletion of the α-1,6 fucosyl transferase gene FUT8 to prevent the addition of α-1,6 fucose and is therefore afucosylated. These antibody preparations were compared in NK-cell mediated antibody-dependent cellular cytotoxicity (ADCC) assays.

Different concentrations of anti-EphA3 antibody preparations were incubated with leukemia primary target cells and normal human PBMC effector cells (Buffy coat from Stanford University Blood Bank). Both fucosylated Antibody 1 and afucosylated Antibody 1 at 0.0001 μg/mL to 10.0 μg/mL were tested with $1\times10^4$ target cells from a patient with acute myeloid leukemia (AML) and $1\times10^6$ normal PBMC effector cells (100:1 effector:target cell ratio). After 16 hours incubation at 37° C., 5% $CO_2$, LDH release was measured in comparison with LDH from detergent-lysed cells to determine the percent cytotoxicity (using a Promega Cytotox 96 kit).

Figure 6:
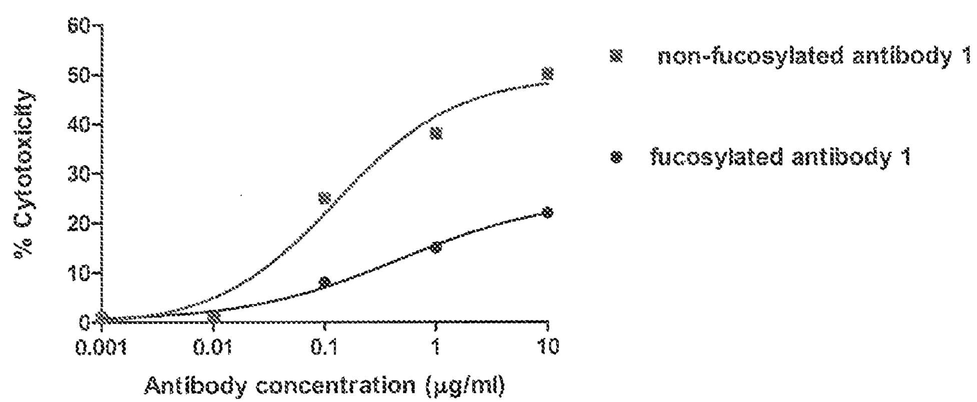
FIG. 6 provides data showing that an afucosylated anti-EphA3 antibody has enhanced ADCC activity against AML cells compared with the fucosylated anti-EphA3 antibody.

Afucosylated Antibody 1 shows increased ADCC activity against EphA3-positive target cells compared with fucosylated Antibody 1 (FIG. 6).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Exemplary $V_H$ Region Sequences of Anti-EphA3 Antibodies of the Invention:

SEQ ID NO: 1

QVQLVQSGAEVKKPGTSVKVSCKASGYTFTGYWMNWVRQASGQGLEWMGD

IYPGSGNTNYDEKFQGRVTMTRDTSISTAYMELSRLRSDDTAVYYCARSG

VYEDFDSWGQGTTVTVSS

SEQ ID NO: 2

QVQLVQSGAEVKKPGASVKVSCKASGYTFTGYWMNWVRQAPGQGLEWMGD

IYPGSGNTNYDEKFQGRVTMTRDTSISTAYMELSRLRSDDTAVYYCARSG

YYEEFDSWGQGTTVTVSS

SEQ ID NO: 3
QVQLVQSGAEVKKPGTSVKVSCKASGYTFTGYWMNWVRQASGQGLEWMGD
IYPGSGNTNYDEKFQGRVTMTRDTSISTAYMELSRLRSDDTAVYYCARSG
YYEEFDSWGQGTTVTVSS

SEQ ID NO: 4
QVQLVQSGAELKKPGASVKVSCKTSGYTFTGYWMNWVRQAPGQGLEWMGD
IYPGSGNTNYDEKFQGRVTMTRDTSISTAYMELSRLRSDDTAVYYCARSG
YYEEFDSWGQGTTVTVSS

SEQ ID NO: 5
QVQLVQSGAEVKKPGASVKVSCKASGYTFTGYWMNWVRQAPGQGLEWMGD
IYPGSGNTNYDEKFQGRVTMTRDTSISTAYMELSRLRSDDTAVYYCARGG
YYEDFDSWGQGTTVTVSS

SEQ ID NO: 6
EVQLVQSGAEVKKPGESLRISCKGSGYTFTTYWISWVRQMPGQGLEWMGD
IYPGSGNTNYAQKFQGRVTITADKSTSTAYMGLSSLRSEDTAVYYCARSG
YYEDFDSWGQGTTVTVSS

SEQ ID NO: 7
EVQLVQSGAEVKKPGESLRISCKGSGYTFTTYWISWVRQMPGQGLEWMGD
IYPGSGNTNYAQEFRGRVTITADESTSTAYVELSSLRSEDTAVYYCARSG
YYEDFDSWGQGTTVTVSS

SEQ ID NO: 8
EVQLVQSGAEVKKPGESLRISCKGSGYTFTTYWISWVRQMPGQGLEWMGD
IYPGSGNTNYAQKFLGRVTITADESTSTAYMELSSLRYDDTAVYYCARSG
YYEDFDSWGQGTTVTVSS

SEQ ID NO: 9
EVKLEESGAELVKPGSSVKLSCKASGYNFTSYWINWVRLRPGQGLEWIGD
IYPGSGNTNYDEKFKRKATLTVDTSSSTAYMQLSSLASEDTAVYYCARSG
YYEDFDVWGQGTTVTVSS

SEQ ID NO: 10
EVKLEESGAELVKPGSSVKLSCKASGYNFTSYWINWVRLRPGQGLEWIGD
IYPGSGNTNYDEKFKRKATLTVDTSSSTAYMQLSSLASEDTAVYYCARSG
YYEDFDIWGQGTMVTVSS

Exemplary $V_L$ Region Sequences of Anti-EphA3 Antibodies of the Invention:

SEQ ID NO: 11
DIQMTQSPSFLSASVGDRVTITCRASQGIISYLAWYQQKPEKAPKRLIYA
ASSLQSGVPSRFSGSGSGTEFTLTISSLQPEDFATYYCVQYANYPYTFGQ
GTKLEIK

SEQ ID NO: 12
DIQMTQSPSFLSASVGDRVTITCRASQGIISYLAWYQQKPEKAPKRLIYA
ASSLQSGVPSRFSGSGSGTEFTLTISSLQPEDFATYYCVQYSNYPYTFGQ
GTKLEIK

SEQ ID NO: 13
DIQMTQSPSFLSASVGDRVTITCRASQGIISYLAWYQQKPEKAPKRLIYA
ASSLQSGVPSRFSGSGSGTEFTLTISSLQPEDFATYYCGQYANYPYTFGQ
GTKLEIK

SEQ ID NO: 14
DIQMTQSPSFLSASVGDRVTITCRASQGIISYLAWYQQKPEKAPKRLIYA
ASSLQSGVPSRFSGSGSGTEFTLTISSLQPEDFATYYCVQYANYPYTFGQ
GTKLEIK

SEQ ID NO: 15
DIQLTQSPSFLSASVGDRVTITCRASQGIISYLAWYQQKPEKAPKRLIYG
ASSLQSGVPSRFSGSGSGTEFTLTISSLQPEDFATYYCVQYANYPYTFGQ
GTKLEIK

SEQ ID NO: 16
DIQMTQSPSSLSASLGDRVTITCQASQDISTYLNWIQQKPGKAPKRLIYA
ASSLQSGVPSRFSGSGSGTEFTLTISSLQPEDFATYYCVQYANYPYTFGQ
GTKLEIK

SEQ ID NO: 17
DIQMTQSPSSLSASLGDRVTITCQASQDISTYLNWIQQKPGKAPKRLIYA
ASSLQRGVPSRFSGSGSGTEFTLTISSLQPEDFATYYCVQYANYPYTFGQ
GTKLEIK

SEQ ID NO: 18
DIQMTQSPSSLSASVGDRVTITCRASQSISSYLAWYQQKPGKAPKRLIYA
ASSLQRGVPSRFSGSGSGTEFTLTISSLQPEDFATYYCVQYANYPYTFGQ
GTKLEIK

SEQ ID NO: 19
DIQMTQSPSFLSASVGDRVTITCRASQGIISYLAWYQQKPEKAPKRLIYA
ASSLQSGVPSRFSGSGSGTEFTLTISSLQPEDFATYYCAQYANYPYTFGQ
GTKLEIK

SEQ ID NO: 20
DIQMTQSPSFLSASVGDRVTITCRASQGIISYLAWYQQKPEKAPKRLIYA
ASSLQSGVPSRFSGSGSGTEFTLTISSLQPEDFATYYCVQYAKYPYTFGQ
GTKLEIK

SEQ ID NO: 21
DIQMTQSPSFLSASVGDRVTITCRASQGIISYLAWYQQKPEKAPKRLIYA
ASSLQSGVPSRFSGSGSGTEFTLTISSLQPEDFATYYCVGYANYPYTFGQ
GTKLEIK

SEQ ID NO: 22
DIQMTQSPSFLSASVGDRVTITCRASQGIISYLAWYQQKPEKAPKRLIYA
ASSLQSGVPSRFSGSGSGTEFTLTISSLQPEDFATYYCVRYANYPYTFGQ
GTKLEIK

SEQ ID NO: 23
DIQMTQSPSFLSASVGDRVTITCRASQGIISYLAWYQQKPEKAPKRLIYA
ASSLQSGVPSRFSGSGSGTEFTLTISSLQPEDFATYYCVQYLNYPYTFGQ
GTKLEIK

SEQ ID NO: 24:
Exemplary heavy chain constant region
ASTKGPSVFPLAPSSKSTSGGTAALGCLVKDYFPEPVTVSWNSGALTSGV -continued

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

SEQ ID NO: 25:
Exemplary light chain constant region
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Exemplary Antibodies of the Invention (Heavy Chain and Light Chain Sequences):

SEQ ID NO: 26
(heavy chain, antibody comprising
SEQ ID NO: 26/27)
QVQLVQSGAEVKKPGASVKVSCKASGYTFTGYWMNWVRQAPGQGLEWMGD

IYPGSGNTNYDEKFQGRVTMTRDTSISTAYMELSRLRSDDTAVYYCARSG

YYEEFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 27
(light chain, antibody comprising
SEQ ID NO: 26/27)
DIQMTQSPSFLSASVGDRVTITCRASQGIISYLAWYQQKPEKAPKRLIYA

ASSLQSGVPSRFSGSGSGTEFTLTISSLQPEDFATYYCVQYANYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 28
(heavy chain, antibody comprising
SEQ ID NO: 28/29)
QVQLVQSGAEVKKPGTSVKVSCKASGYTFTGYWMNWVRQASGQGLEWMGD

IYPGSGNTNYDEKFQGRVTMTRDTSISTAYMELSRLRSDDTAVYYCARSG

VYEDFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

-continued

SEQ ID NO: 29
(light chain, antibody comprising
SEQ ID NO: 28/29)
DIQMTQSPSFLSASVGDRVTITCRASQGIISYLAWYQQKPEKAPKRLIYA

ASSLQSGVPSRFSGSGSGTEFTLTISSLQPEDFATYYCVQYAKYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 30
(heavy chain, antibody comprising
SEQ ID NO: 30/31)
QVQLVQSGAEVKKPGASVKVSCKASGYTFTGYWMNWVRQAPGQGLEWMGD

IYPGSGNTNYDEKFQGRVTMTRDTSISTAYMELSRLRSDDTAVYYCARGG

YYEDFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 31
(light chain, antibody comprising
SEQ ID NO: 30/31)
DIQMTQSPSFLSASVGDRVTITCRASQGIISYLAWYQQKPEKAPKRLIYA

ASSLQSGVPSRFSGSGSGTEFTLTISSLQPEDFATYYCGQYANYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 32
(heavy chain, antibody comprising
SEQ ID NO: 32/33)
QVQLVQSGAEVKKPGTSVKVSCKASGYTFTGYWMNWVRQASGQGLEWMGD

IYPGSGNTNYDEKFQGRVTMTRDTSISTAYMELSRLRSDDTAVYYCARSG

YYEEFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 33
(light chain, antibody comprising
SEQ ID NO: 32/33)
DIQMTQSPSFLSASVGDRVTITCRASQGIISYLAWYQQKPEKAPKRLIYA

ASSLQSGVPSRFSGSGSGTEFTLTISSLQPEDFATYYCVQYANYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

-continued

SEQ ID NO: 34

(heavy chain, antibody comprising SEQ ID NO: 34/35)

QVQLVQSGAEVKKPGASVKVSCKASGYTFTGYWMNWVRQAPGQGLEWMGD

IYPGSGNTNYDEKFQGRVTMTRDTSISTAYMELSRLRSDDTAVYYCARSG

YYEEFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 35

(light chain, antibody comprising SEQ ID NO: 34/35)

DIQMTQSPSFLSASVGDRVTITCRASQGIISYLAWYQQKPEKAPKRLIYA

ASSLQSGVPSRFSGSGSGTEFTLTISSLQPEDFATYYCAQYANYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

-continued

SEQ ID NO: 36

(heavy chain, antibody comprising SEQ ID NO: 36/37)

EVQLVQSGAEVKKPGESLRISCKGSGYTFTTYWISWVRQMPGQGLEWMGD

IYPGSGNTNYAQEFRGRVTITADESTSTAYVELSSLRSEDTAVYYCARSG

YYEDFDSWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 37

(light chain, antibody comprising SEQ ID NO: 36/37)

DIQLTQSPSFLSASVGDRVTITCRASQGIISYLAWYQQKPEKAPKRLIYG

ASSLQSGVPSRFSGSGSGTEFTLTISSLQPEDFATYYCVQYANYPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

---

What is claimed is:

1. An anti-EphA3 antibody, comprising:

a $V_H$ region that comprises a CDR3 having the amino acid sequence GGYYEDFDS (SEQ ID NO:43), SGYYEEFDS (SEQ ID NO:41), SGVYEDFDS (SEQ ID NO:44), SGYYEDFDS (SEQ ID NO:39), SGYYEDFDV (SEQ ID NO:45), or SGYYEDFDI (SEQ ID NO:46);

a CDR2 having the amino acid sequence DIYPGSGNTNYDEKFQG (SEQ ID NO:49); and a CDR1 having the amino acid sequence GYWMN (SEQ ID NO:48); and a $V_L$ region that comprises a CDR3 having the amino acid sequence GQYANYPYT (SEQ ID NO:57), VQYANYPYT (SEQ ID NO:61), VQYSNYPYT (SEQ ID NO:60), AQYANYPYT (SEQ ID NO:59), VQYAKYPYT (SEQ ID NO:58), VGYANYPYT (SEQ ID NO:62), VRYANYPYT (SEQ ID NO:63), or VQYLNYPYT (SEQ ID NO:64);

a CDR2 having the amino acid sequence AASSLQS (SEQ ID NO:68), and a CDR1 having the amino acid sequence RASQGIISYLA (SEQ ID NO:66).

2. The anti-EphA3 antibody of claim 1, wherein the $V_H$ region a FR4 that has the amino acid sequence WGQGTTVTVSS (SEQ ID NO:47).

3. The anti-EphA3 antibody of 1, wherein the CDR3 of the $V_H$ region comprises GGYYEDFDS (SEQ ID NO:43) and the CDR3 of the $V_L$ region comprises GQYANYPYT (SEQ ID NO:57).

4. The anti-EphA3 antibody of claim 1, wherein the $V_H$ region comprises a V-segment having the V-segment amino acid sequence of SEQ ID NO:1, 2, 3, 4, or 5.

5. The anti-EphA3 antibody of claim 4, wherein the $V_H$ region comprises the amino acid sequence of SEQ ID NO:1, 2, 3, 4, or 5.

6. The anti-EphA3 antibody of claim 1, wherein the $V_H$ region comprises a V-segment having the V-segment amino acid sequence of SEQ ID NO:5.

7. The anti-EphA3 antibody of claim 6, wherein the $V_H$ region comprises the amino acid sequence of SEQ ID NO:5.

8. The anti-EphA3 antibody of claim 1, wherein the $V_L$ region comprises a FR4 having the FR4 amino acid sequence FGQGTKLEIK (SEQ ID NO:69).

9. The anti-EphA3 antibody of claim 1, wherein the $V_L$ region comprises a V-segment having the V-segment amino acid sequence of SEQ ID NO:11, 12, 13, 19, 20, 21, 22, or 23.

10. The anti-EphA3 antibody of claim 9, wherein the $V_L$ region comprises the amino acid sequence of SEQ ID NO:11, 12, 13, 19, 20, 21, 22, or 23.

11. The anti-EphA3 antibody of claim 1, wherein the $V_L$ region comprises a V-segment that has the V-segment amino acid sequence of SEQ ID NO:13.

12. The anti-EphA3 antibody of claim 11, wherein the $V_L$ region comprise the amino acid sequence of SEQ ID NO:13.

13. The anti-EphA3 antibody of claim 1, wherein the antibody comprises a $V_H$ region and a $V_L$ region selected from the group consisting of:

a) SEQ ID NO:1 and SEQ ID NO:20,
b) SEQ ID NO:2 and SEQ ID NO:11,
c) SEQ ID NO: 2 and SEQ ID NO:12,
d) SEQ ID NO:2 and SEQ ID NO:19,
e) SEQ ID NO:2 and SEQ ID NO:21,
f) SEQ ID NO:2 and SEQ ID NO:22,
g) SEQ ID NO:2 and SEQ ID NO:23,
h) SEQ ID NO:3 and SEQ ID NO:11,
i) SEQ ID NO:3 and SEQ ID NO:12,
j) SEQ ID NO:3 and SEQ ID NO:21,
k) SEQ ID NO:3 and SEQ ID NO:22,
l) SEQ ID NO:4 and SEQ ID NO:11,
m) SEQ ID NO:4 and SEQ ID NO:13,
n) SEQ ID NO:5 and SEQ ID NO:11,
o) SEQ ID NO:5 and SEQ ID NO:13, and
p) SEQ ID NO:5 and SEQ ID NO:21.

14. The anti-EphA3 antibody of claim 1, wherein the $V_H$ region comprises the amino acid sequence of SEQ ID NO:5 and the $V_L$ region comprises the amino acid sequence of SEQ ID NO:13.

15. The anti-EphA3 antibody of claim 1, wherein the $V_H$ region or the $V_L$ region, or both the $V_H$ and $V_L$ region amino acid sequences comprise a methionine at the N-terminus.

16. The anti-EphA3 antibody of claim 1, wherein the antibody is an IgG.

17. The anti-EphA3 antibody of claim 16, wherein the antibody is a IgG1 or IgG3.

18. The anti-EphA3 antibody of claim 16, wherein the antibody is a IgG2 or IgG4.

19. The anti-EphA3 antibody of claim 16, wherein the antibody comprises a heavy chain constant region having the amino acid sequence set forth in SEQ ID NO:24.

20. The anti-EphA3 antibody of claim 1, wherein the antibody comprises a kappa light chain constant region having the amino acid sequence set forth in SEQ ID NO:25.

21. An anti-EphA3 antibody that has a heavy chain amino acid sequence and a light chain amino acid sequence that comprises SEQ ID NO:26 and SEQ ID NO:27, SEQ ID NO:28 and SEQ ID NO:29, SEQ ID NO:30 and SEQ ID NO:31, SEQ ID NO:32 and SEQ ID NO:33, or SEQ ID NO:34 and SEQ ID NO:35.

22. An antibody preparation comprising the anti-EphA3 antibody of claim 1, wherein the heavy chain constant region is hypofucosylated or afucosylated.

23. The anti-EphA3 antibody of claim 1, wherein the antibody is a $(Fab')_2$.

24. The anti-EphA3 antibody of claim 1, wherein the antibody is PEGylated.

25. The anti-EphA3 antibody of claim 1, wherein the antibody activates EphA3.

26. The anti-EphA3 antibody of claim 1, wherein the antibody has an affinity of better than 10 nM.

27. The anti-EphA3 antibody of claim 26, wherein the antibody has an affinity of better than 1 nM.

28. An anti-EphA3 antibody that has a heavy chain amino acid sequence that comprises SEQ ID NO:30 and a light chain amino acid sequence that comprises and SEQ ID NO:31, wherein the antibody is afucosylated.

29. An antibody preparation comprising the anti-EphA3 antibody of claim 28, wherein the antibody preparation is hypofucosylated.

* * * * *

SEQUENCE LISTING

<160> NUMBER OF SEQ ID NOS: 81

<210> SEQ ID NO 1
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H region

<400> SEQUENCE: 1

```
Gln Val Gln Leu Val Gln Ser Gly Ala Glu Val Lys Lys Pro Gly Thr
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Ser Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Val Tyr Glu Asp Phe Asp Ser Trp Gly Gln Gly Thr
            100                 105                 110

Thr Val Thr Val Ser Ser
        115
```

<210> SEQ ID NO 2
<211> LENGTH: 118

```
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 2

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser
        115


<210> SEQ ID NO 3
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 3

Gln Val Gln Leu Val Gln Ser Gly Ala Glu Val Lys Lys Pro Gly Thr
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Ser Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser
        115


<210> SEQ ID NO 4
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 4

Gln Val Gln Leu Val Gln Ser Gly Ala Glu Leu Lys Lys Pro Gly Ala
 1               5                  10                  15
```

```
Ser Val Lys Val Ser Cys Lys Thr Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser
        115


<210> SEQ ID NO 5
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Tyr Glu Asp Phe Asp Ser Trp Gly Gln Gly Thr
            100                 105                 110

Thr Val Thr Val Ser Ser
        115


<210> SEQ ID NO 6
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 6

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Thr Tyr
            20                  25                  30

Trp Ile Ser Trp Val Arg Gln Met Pro Gly Gln Gly Leu Glu Trp Met
        35                  40                  45

Gly Asp Ile Tyr Pro Gly Ser Gly Asn Thr Asn Tyr Ala Gln Lys Phe
    50                  55                  60
```

```
Gln Gly Arg Val Thr Ile Thr Ala Asp Lys Ser Thr Ser Thr Ala Tyr
65                  70                  75                  80

Met Gly Leu Ser Ser Leu Arg Ser Glu Asp Thr Ala Val Tyr Tyr Cys
                85                  90                  95

Ala Arg Ser Gly Tyr Tyr Glu Asp Phe Asp Ser Trp Gly Gln Gly Thr
            100                 105                 110

Thr Val Thr Val Ser Ser
        115


<210> SEQ ID NO 7
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 7

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Thr Tyr
            20                  25                  30

Trp Ile Ser Trp Val Arg Gln Met Pro Gly Gln Gly Leu Glu Trp Met
        35                  40                  45

Gly Asp Ile Tyr Pro Gly Ser Gly Asn Thr Asn Tyr Ala Gln Glu Phe
    50                  55                  60

Arg Gly Arg Val Thr Ile Thr Ala Asp Glu Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Ser Gly Tyr Tyr Glu Asp Phe Asp Ser Trp Gly Gln Gly Thr
            100                 105                 110

Thr Val Thr Val Ser Ser
        115


<210> SEQ ID NO 8
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 8

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Thr Tyr
            20                  25                  30

Trp Ile Ser Trp Val Arg Gln Met Pro Gly Gln Gly Leu Glu Trp Met
        35                  40                  45

Gly Asp Ile Tyr Pro Gly Ser Gly Asn Thr Asn Tyr Ala Gln Lys Phe
    50                  55                  60

Leu Gly Arg Val Thr Ile Thr Ala Asp Glu Ser Thr Ser Thr Ala Tyr
65                  70                  75                  80

Met Glu Leu Ser Ser Leu Arg Tyr Asp Asp Thr Ala Val Tyr Tyr Cys
                85                  90                  95

Ala Arg Ser Gly Tyr Tyr Glu Asp Phe Asp Ser Trp Gly Gln Gly Thr
            100                 105                 110

Thr Val Thr Val Ser Ser
```

```
        115


<210> SEQ ID NO 9
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 9

Glu Val Lys Leu Glu Glu Ser Gly Ala Glu Leu Val Lys Pro Gly Ser
 1               5                  10                  15

Ser Val Lys Leu Ser Cys Lys Ala Ser Gly Tyr Asn Phe Thr Ser Tyr
            20                  25                  30

Trp Ile Asn Trp Val Arg Leu Arg Pro Gly Gln Gly Leu Glu Trp Ile
        35                  40                  45

Gly Asp Ile Tyr Pro Gly Ser Gly Asn Thr Asn Tyr Asp Glu Lys Phe
    50                  55                  60

Lys Arg Lys Ala Thr Leu Thr Val Asp Thr Ser Ser Ser Thr Ala Tyr
65                  70                  75                  80

Met Gln Leu Ser Ser Leu Ala Ser Glu Asp Thr Ala Val Tyr Tyr Cys
                85                  90                  95

Ala Arg Ser Gly Tyr Tyr Glu Asp Phe Asp Val Trp Gly Gln Gly Thr
            100                 105                 110

Thr Val Thr Val Ser Ser
        115


<210> SEQ ID NO 10
<211> LENGTH: 118
<212> TYPE: PRT
<213> ORGANISM: Artificial Sequence
<220> FEATURE:
<223> OTHER INFORMATION: synthetic anti-EphA3 antibody heavy chain V-H
      region

<400> SEQUENCE: 10

Glu Val Lys Leu Glu Glu Ser Gly Ala Glu Leu Val Lys Pro Gly Ser
 1               5                  10                  15

Ser Val Lys Leu Ser Cys Lys Ala Ser Gly Tyr Asn Phe Thr Ser Tyr
            20                  25                  30

Trp Ile Asn Trp Val Arg Leu Arg Pro Gly Gln Gly Leu Glu Trp Ile
        35                  40                  45

Gly Asp Ile Tyr Pro Gly Ser Gly Asn Thr Asn Tyr Asp Glu Lys Phe
    50                  55                  60

Lys Arg Lys Ala Thr Leu Thr Val Asp Thr Ser Ser Ser Thr Ala Tyr
65                  70                  75                  80

Met Gln Leu Ser Ser Leu Ala Ser Glu Asp Thr Ala Val Tyr Tyr Cys
                85                  90                  95

Ala Arg Ser Gly Tyr Tyr Glu Asp Phe Asp Ile Trp Gly Gln Gly Thr
            100                 105                 110

Met Val Thr Val Ser Ser
        115


<210> SEQ ID NO 11
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region
```

<400> SEQUENCE: 11

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 12

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ser Asn Tyr Pro Tyr
                85                  90                  95

Thr Phe Gly Gln Gly Thr Lys Leu Glu Ile Lys
            100                 105
```

<210> SEQ ID NO 13
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 13

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
65                  70                  75                  80

Glu Asp Phe Ala Thr Tyr Tyr Cys Gly Gln Tyr Ala Asn Tyr Pro Tyr
                85                  90                  95

Thr Phe Gly Gln Gly Thr Lys Leu Glu Ile Lys
            100                 105


<210> SEQ ID NO 14
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region

<400> SEQUENCE: 14

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105


<210> SEQ ID NO 15
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region

<400> SEQUENCE: 15

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105


<210> SEQ ID NO 16
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region
```

<400> SEQUENCE: 16

```
Asp Ile Gln Met Thr Gln Ser Pro Ser Ser Leu Ser Ala Ser Leu Gly
 1               5                  10                  15

Asp Arg Val Thr Ile Thr Cys Gln Ala Ser Gln Asp Ile Ser Thr Tyr
            20                  25                  30

Leu Asn Trp Ile Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105
```

<210> SEQ ID NO 17
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 17

```
Asp Ile Gln Met Thr Gln Ser Pro Ser Ser Leu Ser Ala Ser Leu Gly
 1               5                  10                  15

Asp Arg Val Thr Ile Thr Cys Gln Ala Ser Gln Asp Ile Ser Thr Tyr
            20                  25                  30

Leu Asn Trp Ile Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 18

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
```

```
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105


<210> SEQ ID NO 19
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region

<400> SEQUENCE: 19

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Ala Gln Tyr Ala Asn Tyr Pro Tyr
                85                  90                  95

Thr Phe Gly Gln Gly Thr Lys Leu Glu Ile Lys
            100                 105


<210> SEQ ID NO 20
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region

<400> SEQUENCE: 20

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Lys Tyr Pro Tyr
                85                  90                  95

Thr Phe Gly Gln Gly Thr Lys Leu Glu Ile Lys
            100                 105


<210> SEQ ID NO 21
<211> LENGTH: 107
<212> TYPE: PRT
<213> ORGANISM: Artificial Sequence
<220> FEATURE:
<223> OTHER INFORMATION: synthetic anti-EphA3 antibody light chain V-L
      region
```

<400> SEQUENCE: 21

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gly Tyr Ala Asn Tyr Pro Tyr
                85                  90                  95

Thr Phe Gly Gln Gly Thr Lys Leu Glu Ile Lys
            100                 105
```

<210> SEQ ID NO 22
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 22

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Arg Tyr Ala Asn Tyr Pro Tyr
                85                  90                  95

Thr Phe Gly Gln Gly Thr Lys Leu Glu Ile Lys
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: synthetic anti-EphA3 antibody light chain V-L region

<400> SEQUENCE: 23

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
65                  70                  75                  80

Glu Asp Phe Ala Thr Tyr Tyr Cys Val Gln Tyr Leu Asn Tyr Pro Tyr
                85                  90                  95

Thr Phe Gly Gln Gly Thr Lys Leu Glu Ile Lys
            100                 105


<210> SEQ ID NO 24
<211> LENGTH: 330
<212> TYPE: PRT
<213> ORGANISM: Artificial Sequence
<220> FEATURE:
<223> OTHER INFORMATION: synthetic anti-EphA3 antibody heavy chain
      constant region

<400> SEQUENCE: 24

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

325 330

<210> SEQ ID NO 25
<211> LENGTH: 107
<212> TYPE: PRT
<213> ORGANISM: Artificial Sequence
<220> FEATURE:
<223> OTHER INFORMATION: synthetic anti-EphA3 antibody kappa light chain constant region

<400> SEQUENCE: 25

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 26
<211> LENGTH: 448
<212> TYPE: PRT
<213> ORGANISM: Artificial Sequence
<220> FEATURE:
<223> OTHER INFORMATION: synthetic anti-EphA3 antibody heavy chain

<400> SEQUENCE: 26

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 27
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 27

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 28
<211> LENGTH: 448
<212> TYPE: PRT
<213> ORGANISM: Artificial Sequence
<220> FEATURE:
<223> OTHER INFORMATION: synthetic anti-EphA3 antibody heavy chain

<400> SEQUENCE: 28

Gln Val Gln Leu Val Gln Ser Gly Ala Glu Val Lys Lys Pro Gly Thr
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Ser Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Val Tyr Glu Asp Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 29
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 29

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Lys Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 30
<211> LENGTH: 448
<212> TYPE: PRT
<213> ORGANISM: Artificial Sequence
<220> FEATURE:
<223> OTHER INFORMATION: synthetic anti-EphA3 antibody heavy chain

<400> SEQUENCE: 30

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Tyr Glu Asp Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
```

```
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 31
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 31

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gly Gln Tyr Ala Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 32
<211> LENGTH: 448
<212> TYPE: PRT
<213> ORGANISM: Artificial Sequence
<220> FEATURE:
<223> OTHER INFORMATION: synthetic anti-EphA3 antibody heavy chain
```

<400> SEQUENCE: 32

```
Gln Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Gly Tyr
            20                  25                  30

Trp Met Asn Trp Val Arg Gln Ala Ser Gly Gln Gly Leu Glu Trp Met
        35                  40                  45

Gly Asp Ile Tyr Pro Gly Ser Gly Asn Thr Asn Tyr Asp Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 33
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 33

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 34
<211> LENGTH: 448
<212> TYPE: PRT
<213> ORGANISM: Artificial Sequence
<220> FEATURE:
<223> OTHER INFORMATION: synthetic anti-EphA3 antibody heavy chain

<400> SEQUENCE: 34

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Trp Met Asn Trp Val Arg Gln Ala Pro Gly Gln Gly Leu Glu Trp Met
        35                  40                  45

Gly Asp Ile Tyr Pro Gly Ser Gly Asn Thr Asn Tyr Asp Glu Lys Phe
    50                  55                  60
```

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Glu Glu Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 35
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 35

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Ala Gln Tyr Ala Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 36
<211> LENGTH: 448
<212> TYPE: PRT
<213> ORGANISM: Artificial Sequence
<220> FEATURE:
<223> OTHER INFORMATION: synthetic anti-EphA3 antibody heavy chain

<400> SEQUENCE: 36

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Thr Tyr
            20                  25                  30

Trp Ile Ser Trp Val Arg Gln Met Pro Gly Gln Gly Leu Glu Trp Met
        35                  40                  45

Gly Asp Ile Tyr Pro Gly Ser Gly Asn Thr Asn Tyr Ala Gln Glu Phe
    50                  55                  60

Arg Gly Arg Val Thr Ile Thr Ala Asp Glu Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Ser Gly Tyr Tyr Glu Asp Phe Asp Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 37
<211> LENGTH: 214
<212> TYPE: PRT
<213> ORGANISM: Artificial Sequence
<220> FEATURE:
<223> OTHER INFORMATION: synthetic anti-EphA3 antibody light chain

<400> SEQUENCE: 37

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ile Ser Tyr
            20                  25                  30

Leu Ala Trp Tyr Gln Gln Lys Pro Glu Lys Ala Pro Lys Arg Leu Ile
        35                  40                  45

Tyr Gly Ala Ser Ser Leu Gln Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 38
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3
<220> FEATURE:
<221> NAME/KEY: VARIANT
<222> LOCATION: (1)...(1)
<223> OTHER INFORMATION: Xaa = Ser or Gly
<220> FEATURE:
<221> NAME/KEY: VARIANT
<222> LOCATION: (3)...(3)
<223> OTHER INFORMATION: Xaa = Tyr or Val
<220> FEATURE:
<221> NAME/KEY: VARIANT
<222> LOCATION: (6)...(6)
<223> OTHER INFORMATION: Xaa = Glu or Asp
<220> FEATURE:
<221> NAME/KEY: VARIANT
<222> LOCATION: (9)...(9)
<223> OTHER INFORMATION: Xaa = Ser, Val or Ile

<400> SEQUENCE: 38

Xaa Gly Xaa Tyr Glu Xaa Phe Asp Xaa
 1               5


<210> SEQ ID NO 39
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 39

Ser Gly Tyr Tyr Glu Asp Phe Asp Ser
 1               5


<210> SEQ ID NO 40
<211> LENGTH: 5
<212> TYPE: PRT
<213> ORGANISM: Artificial Sequence
<220> FEATURE:
<223> OTHER INFORMATION: synthetic anti-EphA3 antibody V-H region CDR1
```

<400> SEQUENCE: 40

Ser Tyr Trp Ile Asn
1 5

<210> SEQ ID NO 41
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 41

Ser Gly Tyr Tyr Glu Glu Phe Asp Ser
1 5

<210> SEQ ID NO 42
<211> LENGTH: 5
<212> TYPE: PRT
<213> ORGANISM: Artificial Sequence
<220> FEATURE:
<223> OTHER INFORMATION: synthetic anti-EphA3 antibody V-H region CDR1

<400> SEQUENCE: 42

Thr Tyr Trp Ile Ser
1 5

<210> SEQ ID NO 43
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 43

Gly Gly Tyr Tyr Glu Asp Phe Asp Ser
1 5

<210> SEQ ID NO 44
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 44

Ser Gly Val Tyr Glu Asp Phe Asp Ser
1 5

<210> SEQ ID NO 45
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 45

Ser Gly Tyr Tyr Glu Asp Phe Asp Val
1 5

<210> SEQ ID NO 46
<211> LENGTH: 9
<212> TYPE: PRT
<213> ORGANISM: Artificial Sequence
<220> FEATURE:
<223> OTHER INFORMATION: synthetic anti-EphA3 antibody V-H region CDR3

<400> SEQUENCE: 46

```
Ser Gly Tyr Tyr Glu Asp Phe Asp Ile
 1               5


<210> SEQ ID NO 47
<211> LENGTH: 11
<212> TYPE: PRT
<213> ORGANISM: Artificial Sequence
<220> FEATURE:
<223> OTHER INFORMATION: synthetic anti-EphA3 antibody FR4, humaneered
      Fab Vh-region from human germ-line JH6

<400> SEQUENCE: 47

Trp Gly Gln Gly Thr Thr Val Thr Val Ser Ser
 1               5                   10


<210> SEQ ID NO 48
<211> LENGTH: 5
<212> TYPE: PRT
<213> ORGANISM: Artificial Sequence
<220> FEATURE:
<223> OTHER INFORMATION: synthetic anti-EphA3 antibody V-H region CDR1

<400> SEQUENCE: 48

Gly Tyr Trp Met Asn
 1               5


<210> SEQ ID NO 49
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2

<400> SEQUENCE: 49

Asp Ile Tyr Pro Gly Ser Gly Asn Thr Asn Tyr Asp Glu Lys Phe Gln
 1               5                   10                  15

Gly


<210> SEQ ID NO 50
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2

<400> SEQUENCE: 50

Asp Ile Tyr Pro Gly Ser Gly Asn Thr Asn Tyr Ala Gln Lys Phe Gln
 1               5                   10                  15

Gly


<210> SEQ ID NO 51
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2

<400> SEQUENCE: 51

Asp Ile Tyr Pro Gly Ser Gly Asn Thr Asn Tyr Ala Gln Glu Phe Arg
 1               5                   10                  15

Gly


<210> SEQ ID NO 52
<211> LENGTH: 17
<212> TYPE: PRT
<213> ORGANISM: Artificial Sequence
```

<220> FEATURE:
<223> OTHER INFORMATION: synthetic anti-EphA3 antibody V-H region CDR2

<400> SEQUENCE: 52

```
Asp Ile Tyr Pro Gly Ser Gly Asn Thr Asn Tyr Ala Gln Lys Phe Leu
 1               5                   10                  15

Gly
```

<210> SEQ ID NO 53
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2

<400> SEQUENCE: 53

```
Asp Ile Tyr Pro Gly Ser Gly Asn Thr Asn Tyr Asp Glu Lys Phe Glu
 1               5                   10                  15

Gly
```

<210> SEQ ID NO 54
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2, mIIIA4 heavy chain CDR2

<400> SEQUENCE: 54

```
Asp Ile Tyr Pro Gly Ser Gly Asn Thr Asn Tyr Asp Glu Lys Phe Lys
 1               5                   10                  15

Arg
```

<210> SEQ ID NO 55
<211> LENGTH: 17
<212> TYPE: PRT
<213> ORGANISM: Artificial Sequence
<220> FEATURE:
<223> OTHER INFORMATION: synthetic anti-EphA3 antibody V-H region CDR2
<220> FEATURE:
<221> NAME/KEY: VARIANT
<222> LOCATION: (14)...(14)
<223> OTHER INFORMATION: Xaa = Lys or Glu
<220> FEATURE:
<221> NAME/KEY: VARIANT
<222> LOCATION: (16)...(16)
<223> OTHER INFORMATION: Xaa = Gln, Arg or Leu

<400> SEQUENCE: 55

```
Asp Ile Tyr Pro Gly Ser Gly Asn Thr Asn Tyr Ala Gln Xaa Phe Xaa
 1               5                   10                  15

Gly
```

<210> SEQ ID NO 56
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3 binding specificity determinant
<220> FEATURE:
<221> NAME/KEY: VARIANT
<222> LOCATION: (1)...(1)
<223> OTHER INFORMATION: Xaa = Gly, Val or Ala
<220> FEATURE:
<221> NAME/KEY: VARIANT
<222> LOCATION: (2)...(2)
<223> OTHER INFORMATION: Xaa = Gln, Arg or Gly
<220> FEATURE:
<221> NAME/KEY: VARIANT
<222> LOCATION: (4)...(4)
<223> OTHER INFORMATION: Xaa = Ala, Ser or Leu
<220> FEATURE:
<221> NAME/KEY: VARIANT
<222> LOCATION: (5)...(5)
<223> OTHER INFORMATION: Xaa = Asn or Lys

<400> SEQUENCE: 56

```
Xaa Xaa Tyr Xaa Xaa Tyr Pro Tyr Thr
 1               5
```

<210> SEQ ID NO 57
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 57

```
Gly Gln Tyr Ala Asn Tyr Pro Tyr Thr
 1               5
```

<210> SEQ ID NO 58
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 58

```
Val Gln Tyr Ala Lys Tyr Pro Tyr Thr
 1               5
```

<210> SEQ ID NO 59
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 59

```
Ala Gln Tyr Ala Asn Tyr Pro Tyr Thr
 1               5
```

<210> SEQ ID NO 60
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 60

```
Val Gln Tyr Ser Asn Tyr Pro Tyr Thr
 1               5
```

<210> SEQ ID NO 61
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 61

```
Val Gln Tyr Ala Asn Tyr Pro Tyr Thr
 1               5
```

<210> SEQ ID NO 62
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 62

Val Gly Tyr Ala Asn Tyr Pro Tyr Thr
1 5

<210> SEQ ID NO 63
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 63

Val Arg Tyr Ala Asn Tyr Pro Tyr Thr
1 5

<210> SEQ ID NO 64
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 64

Val Gln Tyr Leu Asn Tyr Pro Tyr Thr
1 5

<210> SEQ ID NO 65
<211> LENGTH: 11
<212> TYPE: PRT
<213> ORGANISM: Artificial Sequence
<220> FEATURE:
<223> OTHER INFORMATION: synthetic anti-EphA3 antibody V-L region CDR1

<400> SEQUENCE: 65

Arg Ala Ser Gln Glu Ile Ser Gly Tyr Leu Gly
1 5 10

<210> SEQ ID NO 66
<211> LENGTH: 11
<212> TYPE: PRT
<213> ORGANISM: Artificial Sequence
<220> FEATURE:
<223> OTHER INFORMATION: synthetic anti-EphA3 antibody V-L region CDR1

<400> SEQUENCE: 66

Arg Ala Ser Gln Gly Ile Ile Ser Tyr Leu Ala
1 5 10

<210> SEQ ID NO 67
<211> LENGTH: 7
<212> TYPE: PRT
<213> ORGANISM: Artificial Sequence
<220> FEATURE:
<223> OTHER INFORMATION: synthetic anti-EphA3 antibody V-L region CDR2

<400> SEQUENCE: 67

Ala Ala Ser Thr Leu Asp Ser
1 5

<210> SEQ ID NO 68
<211> LENGTH: 7

```
<212> TYPE: PRT
<213> ORGANISM: Artificial Sequence
<220> FEATURE:
<223> OTHER INFORMATION: synthetic anti-EphA3 antibody V-L region CDR2

<400> SEQUENCE: 68

Ala Ala Ser Ser Leu Gln Ser
 1               5


<210> SEQ ID NO 69
<211> LENGTH: 10
<212> TYPE: PRT
<213> ORGANISM: Artificial Sequence
<220> FEATURE:
<223> OTHER INFORMATION: synthetic human germ-line Jkappa2, anti-EphA3
      antibody FR4, humaneered Fab Vk region from
      human germ-line Jkappa2

<400> SEQUENCE: 69

Phe Gly Gln Gly Thr Lys Leu Glu Ile Lys
 1               5                   10


<210> SEQ ID NO 70
<211> LENGTH: 11
<212> TYPE: PRT
<213> ORGANISM: Artificial Sequence
<220> FEATURE:
<223> OTHER INFORMATION: synthetic anti-EphA3 antibody V-L region CDR1

<400> SEQUENCE: 70

Gln Ala Ser Gln Asp Ile Ser Thr Tyr Leu Asn
 1               5                   10


<210> SEQ ID NO 71
<211> LENGTH: 11
<212> TYPE: PRT
<213> ORGANISM: Artificial Sequence
<220> FEATURE:
<223> OTHER INFORMATION: synthetic anti-EphA3 antibody V-L region CDR1

<400> SEQUENCE: 71

Arg Ala Ser Gln Ser Ile Ser Ser Tyr Leu Ala
 1               5                   10


<210> SEQ ID NO 72
<211> LENGTH: 7
<212> TYPE: PRT
<213> ORGANISM: Artificial Sequence
<220> FEATURE:
<223> OTHER INFORMATION: synthetic anti-EphA3 antibody V-L region CDR2

<400> SEQUENCE: 72

Gly Ala Ser Ser Leu Gln Ser
 1               5


<210> SEQ ID NO 73
<211> LENGTH: 7
<212> TYPE: PRT
<213> ORGANISM: Artificial Sequence
<220> FEATURE:
<223> OTHER INFORMATION: synthetic anti-EphA3 antibody V-L region CDR2

<400> SEQUENCE: 73

Ala Ala Ser Ser Leu Gln Arg
 1               5


<210> SEQ ID NO 74
<211> LENGTH: 9
```

```
<212> TYPE: PRT
<213> ORGANISM: Artificial Sequence
<220> FEATURE:
<223> OTHER INFORMATION: synthetic anti-EphA3 antibody V-H region CDR3
<220> FEATURE:
<221> NAME/KEY: VARIANT
<222> LOCATION: (6)...(6)
<223> OTHER INFORMATION: Xaa = Glu or Asp

<400> SEQUENCE: 74

Ser Gly Tyr Tyr Glu Xaa Phe Asp Ser
 1               5


<210> SEQ ID NO 75
<211> LENGTH: 9
<212> TYPE: PRT
<213> ORGANISM: Artificial Sequence
<220> FEATURE:
<223> OTHER INFORMATION: synthetic anti-EphA3 antibody V-L region CDR3

<400> SEQUENCE: 75

Val Gln Tyr Met Asn Tyr Pro Tyr Thr
 1               5


<210> SEQ ID NO 76
<211> LENGTH: 17
<212> TYPE: PRT
<213> ORGANISM: Artificial Sequence
<220> FEATURE:
<223> OTHER INFORMATION: synthetic human germ-line Vh1-58 CDR2

<400> SEQUENCE: 76

Trp Ile Val Val Gly Ser Gly Asn Thr Asn Tyr Ala Gln Lys Phe Gln
 1               5                   10                  15

Glu


<210> SEQ ID NO 77
<211> LENGTH: 11
<212> TYPE: PRT
<213> ORGANISM: Artificial Sequence
<220> FEATURE:
<223> OTHER INFORMATION: synthetic human Vh1 partial sequence

<400> SEQUENCE: 77

Asp Ile Tyr Pro Gly Ser Gly Asn Thr Asn Tyr
 1               5                   10


<210> SEQ ID NO 78
<211> LENGTH: 118
<212> TYPE: PRT
<213> ORGANISM: Artificial Sequence
<220> FEATURE:
<223> OTHER INFORMATION: synthetic murine mIIIA4 and reference Fab FA4
      Vh region

<400> SEQUENCE: 78

Glu Val Lys Leu Glu Glu Ser Gly Ala Glu Leu Val Lys Pro Gly Ser
 1               5                   10                  15

Ser Val Lys Leu Ser Cys Lys Ala Ser Gly Tyr Asn Phe Thr Ser Tyr
            20                  25                  30

Trp Ile Asn Trp Val Arg Leu Arg Pro Gly Gln Gly Leu Glu Trp Ile
        35                  40                  45

Gly Asp Ile Tyr Pro Gly Ser Gly Asn Thr Asn Tyr Asp Glu Lys Phe
    50                  55                  60

Lys Arg Lys Ala Thr Leu Thr Val Asp Thr Ser Ser Ser Thr Ala Tyr
65                  70                  75                  80
```

```
Met Gln Leu Ser Ser Leu Ala Ser Glu Asp Ser Ala Leu Tyr Tyr Cys
                85                  90                  95

Thr Arg Ser Gly Tyr Tyr Glu Asp Phe Asp Ser Trp Gly Gln Gly Thr
            100                 105                 110

Thr Leu Ile Val Ser Ser
        115


<210> SEQ ID NO 79
<211> LENGTH: 107
<212> TYPE: PRT
<213> ORGANISM: Artificial Sequence
<220> FEATURE:
<223> OTHER INFORMATION: synthetic murine mIIIA4 and reference Fab FA4
      Vk region

<400> SEQUENCE: 79

Asp Ile Val Leu Thr Gln Thr Pro Ser Ser Leu Ser Ala Ser Leu Glu
 1               5                  10                  15

Glu Arg Val Ser Leu Thr Cys Arg Ala Ser Gln Glu Ile Ser Gly Tyr
            20                  25                  30

Leu Gly Trp Leu Gln Gln Lys Pro Asp Gly Thr Ile Lys Arg Leu Ile
        35                  40                  45

Tyr Ala Ala Ser Thr Leu Asp Ser Gly Val Pro Lys Lys Phe Ser Gly
    50                  55                  60

Asn Arg Ser Gly Ser Glu Tyr Ser Leu Thr Ile Ser Ser Leu Glu Ser
65                  70                  75                  80

Glu Asp Phe Ala Asp Tyr Tyr Cys Val Gln Tyr Ala Asn Tyr Pro Tyr
                85                  90                  95

Thr Phe Gly Gly Gly Thr Lys Leu Glu Ile Lys
            100                 105


<210> SEQ ID NO 80
<211> LENGTH: 118
<212> TYPE: PRT
<213> ORGANISM: Artificial Sequence
<220> FEATURE:
<223> OTHER INFORMATION: synthetic optimized reference Fab FA106 Vh
      region

<400> SEQUENCE: 80

Glu Val Lys Leu Glu Glu Ser Gly Ala Glu Leu Val Lys Pro Gly Ser
 1               5                  10                  15

Ser Val Lys Leu Ser Cys Lys Ala Ser Gly Tyr Asn Phe Thr Ser Tyr
            20                  25                  30

Trp Ile Asn Trp Val Arg Leu Arg Pro Gly Gln Gly Leu Glu Trp Ile
        35                  40                  45

Gly Asp Ile Tyr Pro Gly Ser Gly Asn Thr Asn Tyr Asp Glu Lys Phe
    50                  55                  60

Lys Arg Lys Ala Thr Leu Thr Val Asp Thr Ser Ser Ser Thr Ala Tyr
65                  70                  75                  80

Met Gln Leu Ser Ser Leu Ala Ser Glu Asp Thr Ala Val Tyr Tyr Cys
                85                  90                  95

Ala Arg Ser Gly Tyr Tyr Glu Asp Phe Asp Ser Trp Gly Gln Gly Thr
            100                 105                 110

Thr Val Thr Val Ser Ser
         115


<210> SEQ ID NO 81
<211> LENGTH: 107
```

```
<212> TYPE: PRT
<213> ORGANISM: Artificial Sequence
<220> FEATURE:
<223> OTHER INFORMATION: synthetic optimized reference Fab FA106 Vk
      region

<400> SEQUENCE: 81

Asp Ile Val Leu Thr Gln Thr Pro Ser Ser Leu Ser Ala Ser Leu Glu
 1               5                  10                  15

Glu Arg Val Ser Leu Thr Cys Arg Ala Ser Gln Glu Ile Ser Gly Tyr
            20                  25                  30

Leu Gly Trp Leu Gln Gln Lys Pro Asp Gly Thr Ile Lys Arg Leu Ile
        35                  40                  45

Tyr Ala Ala Ser Thr Leu Asp Ser Gly Val Pro Lys Lys Phe Ser Gly
    50                  55                  60

Asn Arg Ser Gly Ser Glu Tyr Ser Leu Thr Ile Ser Ser Leu Glu Ser
65                  70                  75                  80

Glu Asp Phe Ala Thr Tyr Tyr Cys Val Gln Tyr Ala Asn Tyr Pro Tyr
                85                  90                  95

Thr Phe Gly Gln Gly Thr Lys Leu Glu Ile Lys
            100                 105
```